United States Patent
Lee et al.

(10) Patent No.: US 12,195,759 B2
(45) Date of Patent: Jan. 14, 2025

(54) MODIFIED NATURAL KILLER CELLS, PHARMACEUTICAL COMPOSITION, MANUFACTURING METHOD THEREOF, AND METHOD OF USING THE SAME

(71) Applicant: FULLHOPE BIOMEDICAL CO., LTD., New Taipei (TW)

(72) Inventors: Jan-Mou Lee, New Taipei (TW); Chih-Hao Fang, New Taipei (TW); Ya-Fang Cheng, New Taipei (TW); Pei-Yu Chou, New Taipei (TW)

(73) Assignee: FULLHOPE BIOMEDICAL CO., LTD., New Taipei (TW)

( * ) Notice: Subject to any disclaimer, the term of this patent is extended or adjusted under 35 U.S.C. 154(b) by 317 days.

(21) Appl. No.: 16/797,550

(22) Filed: Feb. 21, 2020

(65) Prior Publication Data

US 2021/0260115 A1    Aug. 26, 2021

(51) Int. Cl.
  *A61K 35/17*   (2015.01)
  *A61K 39/00*   (2006.01)
  *C12N 5/077*   (2010.01)
  *C12N 5/0775*   (2010.01)
  *C12N 5/0783*   (2010.01)

(52) U.S. Cl.
  CPC ........ *C12N 5/0665* (2013.01); *A61K 39/4613* (2023.05); *A61K 39/4644* (2023.05); *C12N 5/0638* (2013.01); *C12N 5/0646* (2013.01); *C12N 5/0669* (2013.01); *C12N 2501/2312* (2013.01); *C12N 2501/2315* (2013.01); *C12N 2501/2318* (2013.01)

(58) Field of Classification Search
  CPC ............ A61K 35/17; C12N 2501/2312; C12N 2501/2315; C12N 2501/2318
  See application file for complete search history.

(56) References Cited

U.S. PATENT DOCUMENTS

2018/0346877 A1   12/2018   Zhang et al.

FOREIGN PATENT DOCUMENTS

| JP | 2013-532469 A | 8/2013 |
| WO | WO2012/009422 A1 | 1/2012 |
| WO | WO2015/100495 A1 | 7/2015 |
| WO | WO2019/165121 A1 | 8/2019 |

OTHER PUBLICATIONS

Leong et al. Preactivation with IL-12, IL-15, and IL-18 induces CD25 and a functional high-affinity IL-2 receptor on human cytokine-induced memory-like natural killer cells, Biol Blood Marrow Transplant, 20: 463-473. (Year: 2014).*
Poli et al. CD56bright natural killer (NK) cells: an important NK cell subset, Immunology, 126, 458-465. (Year: 2009).*
Chidrawar et al., Ageing is associated with a decline in peripheral blood CD56bright NK cells, Immunity and Ageing, 3(10): 1-8 (Year: 2006).*
Loza et al., The IL-12 Signature: NK Cell Terminal CD56high Stage and Effector Functions, The Journal of Immunology, 172(1): 88-96. (Year: 2004).*
Summers et al., (Phenotypic Characterization of Five Dendritic Cell Subsets in Human Tonsils, American Journal of Pathology, 159(1): 2001. (Year: 2001).*
MIchael et al., Human CD56bright NK Cells: An Update, The Journal of Immunology, 196(7): 2923-2931. (Year: 2016).*
Erokhina et al., HLA-DR-expressing NK cells: Effective killers suspected for antigen presentation, 10(9): 327-337. (Year: 2020).*
Ju et al., The Analysis of CD83 Expression on Human Immune Cells Identifies a Unique CD83+-Activated T Cell Population, The Journal of Immunology, 197(12): 4613-4625. (Year: 2016).*
McInnis et al., The role of interleukin-IS in T-cell migration and activation in rheumatoid arthritis, Nature Medicine, 2(2): 175-182. (Year: 1996).*
Kim et al., The role of IL-12 in inflammatory activity of patients with rheumatoid arthritis (RA), Clinical and Experimental Immunology, 119: 175-181. (Year: 2000).*
Gracie et al., A proinflammatory role for IL-18 in rheumatoid arthritis, The Journal of Clinical Investigation, 104(10): 1393-1401. (Year: 1999).*
Fehniger et al., Differential Cytokine and Chemokine Gene Expression by Human NK Cells Following Activation with IL-18 or IL-15 in Combination with IL-12: Implications for the Innate Immune Response, The Journal of Immunology, 162: 4511-4520. (Year: 1999).*
Kleiveland, Peripheral Blood Mononuclear Cells, Chapter 15 in The Impact of Food Bio-Actives on Gut Health, p. 161-167. (Year: 2015).*
Valley Biomedical, Human AB Serum, retrieved from internet Jul. 5, 2024. (Year: 2024).*
Fu et al., Memory-Like Antigen-Specific Human NK Cells from TB Pleural Fluids Produced IL-22 in Response to IL-15 or *Mycobacterium tuberculosis* Antigens, Plos One, p. 1-16. (Year: 2016).*
Zhang et al., Interleukin-12 improves cytotoxicity of natural killer cells via upregulated expression of NKG2D, Immunology, 69: 490-500. (Year: 2008).*
Extended European Search Report for European Patent App. No. 21158251.5 (Jul. 9, 2021).
Fehniger, T.A., et al., "Differential Cytokine and Chemokine Gene Expression by Human NK Cells Following Activation with IL-18 or IL-15 in Combination with IL-12: Implications for the Innate Immune Response," J. Immunol. 1999;162:4511-4520.
Yang, C., et al., "Overview of Strategies to Improve Therapy against Tumors Using Natural Killer Cell," J. Immunol. Res. 2020; Article ID 8459496; 1-16.

(Continued)

*Primary Examiner* — Arthur S Leonard
*Assistant Examiner* — Joseph Paul Miano
(74) *Attorney, Agent, or Firm* — Cermak & McGowan LLP; Shelly Guest Cermak

(57) ABSTRACT

This disclosure provides modified natural killer (NK) cells possessing both NK cell function and dendritic cell function and method of culturing the same. By administration of the modified NK cell, cancer cells in a subject may be effectively inhibited via cell-mediated immunity.

12 Claims, 43 Drawing Sheets

(56) References Cited

OTHER PUBLICATIONS

Senju, H., et al., "Effect of IL-18 on the Expansion and Phenotype of Human Natural Killer Cells: Application to Cancer Immunotherapy," Int. J. Biol. Sci. 2018;14:331-340.
Notice of Reasons for Rejection for Japanese Patent App. No. 2020-210259 (Jul. 16, 2024) with English language translation thereof.

* cited by examiner

G1
(X-vivo 20)

G2
(X-vivo 20)
HPL

G3
(AIM-V)

G4
(AIM-V)
HPL

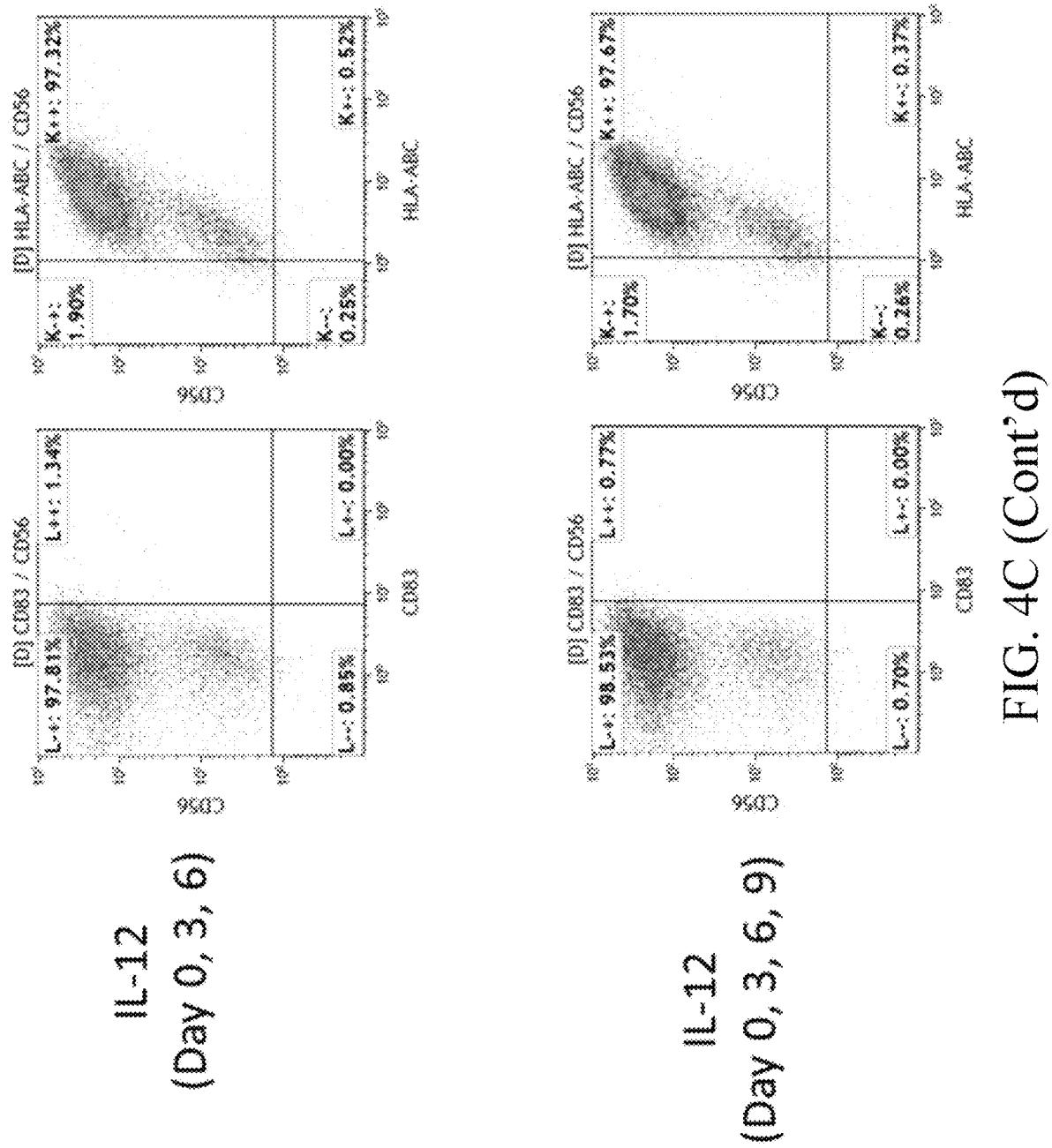

Target (K562) ←---------- w/o IL-18

Day 9

Day 12

Day 15 w IL-18
(Day 0, 3, 6)

MODIFIED NATURAL KILLER CELLS, PHARMACEUTICAL COMPOSITION, MANUFACTURING METHOD THEREOF, AND METHOD OF USING THE SAME

FIELD OF INVENTION

The disclosure relates to modified natural killer (NK) cells and pharmaceutical compositions comprising the same. Methods are also provided for identifying the modified NK cells and culturing of the modified NK cells.

BACKGROUND OF THE INVENTION

Immune surveillance plays a critical role against cancer and represents a very attractive therapeutic approach, especially in light of the many shortcomings of conventional surgery, radiation and chemotherapies in the management of cancer.

The human body's first line of defense against cancer is the natural killer (NK) cell, with the phenotype of $CD3^-CD14^-CD19^-CD56^+CD16^+NGK2D^+CD11c^{dim}HLA-DR^-CD86^-CD83^-$. NK cells are cytotoxic lymphocytes that actively scan the body for abnormal cells, destroying them before they can develop into actual cancer cells. As NK cells patrol the body, they interact with many types of cells using their array of activating and inhibiting surface receptors. Most cancer cells engage the NK cell's activating receptors, which triggers its natural kill response.

These findings support a rationale for develop a NK based therapy against cancer cells and culture methods to generate greater number of therapeutically competent NK cells for clinical applications, as there is still an unmet need for effective treatment and/or prevention for cancer. The present disclosure provides modified natural killer cells having a unique phenotype to satisfy these and other needs. The cells can be used in autologous therapy or in non-autologous therapy.

SUMMARY OF THE INVENTION

In view of the urgent need of the art, provided herein are modified natural killer (NK) cells and pharmaceutical compositions comprising the same that are safe and effective in the treatment of the cancer.

In one embodiment, the present disclosure provides a modified NK cell comprising a phenotype of $CD45^+CD3^-CD19^-CD14^-$. In a preferred embodiment, the modified NK cell may further comprise a phenotype of $CD56^{hi}CD16^{dim}NKG2D^+CD11c^+CD86^+HLA-DR^+CD83^-HLA-ABC^+$, i.e. the modified NK cell may comprise a phenotype of $CD45^+CD3^-CD19^-CD14^-CD56^{hi}CD16^{dim}NKG2D^+CD11c^+CD86^+HLA-DR^+CD83^-HLA-ABC^+$.

Some embodiments provide pharmaceutical compositions comprising a modified NK cell described herein and a pharmaceutically acceptable carrier or excipient.

Some embodiments provide a method of treating cancer cells, comprising administering an effective amount of modified NK cells or pharmaceutical compositions as described herein to a subject in need thereof.

In a preferred embodiment, the effective amount may be about $1\times10^3$ to about $1\times10^9$ cells per dose.

In a preferred embodiment, the modified NK cell may be autologous or allogeneic.

In a preferred embodiment, the modified NK cell may be derived from peripheral blood, cord blood or bone marrow.

In a preferred embodiment, the method may further comprise expanding the modified NK cell in vitro.

Other embodiments provide a method of culturing a modified NK cell possessing both NK cell function and dendritic cell function, comprising
  obtaining a body fluid comprising mononuclear cells;
  contacting the mononuclear cells with a first culturing medium comprising IL-15, IL-12 and IL-18 to obtain a cultured cell population; and
  isolating the modified NK cell with a phenotype of $CD3^-CD19^-CD14^-CD56^{hi}CD16^{dim}NKG2D^+CD11c^+CD86^+HLA-DR^+CD83^-$ from the cultured cell population.

In a preferred embodiment, the mononuclear cells may be derived from peripheral blood, cord blood or bone marrow.

In a preferred embodiment, the first culturing medium may further comprise a hematopoietic cell medium, preferably an AIM-V medium.

In a preferred embodiment, the first culturing medium may further comprise a serum protein, preferably a human platelet lysate.

In a preferred embodiment, the mononuclear cells may be in contact with the first culturing medium for about 1-6 day(s).

In a preferred embodiment, the method may further comprise contacting the cultured cell population with a second culturing medium comprising IL-15 and IL-12 after contacting with the first culturing medium.

In a preferred embodiment, the second culturing medium may further comprise a hematopoietic cell medium, preferably an AIM-V medium.

In a preferred embodiment, the second culturing medium may further comprise a serum protein, preferably a human platelet lysate.

In a preferred embodiment, the cultured cell population may be in contact with the second culturing medium for about 1-6 day(s).

In a preferred embodiment, the method may further comprise negative selecting the mononuclear cells for cells with a phenotype of $CD3^-CD14^-CD19^-$ prior to contacting with the first culturing medium.

The culturing methods described herein allow for isolation of a greater number of modified NK cells from a fixed amount of a sample, for example, 10 mL of blood.

BRIEF DESCRIPTION OF THE DRAWINGS

Illustrative embodiments of the present application are described in detail below with reference to the following figures.

DETAILED DESCRIPTION

Figure 1A:
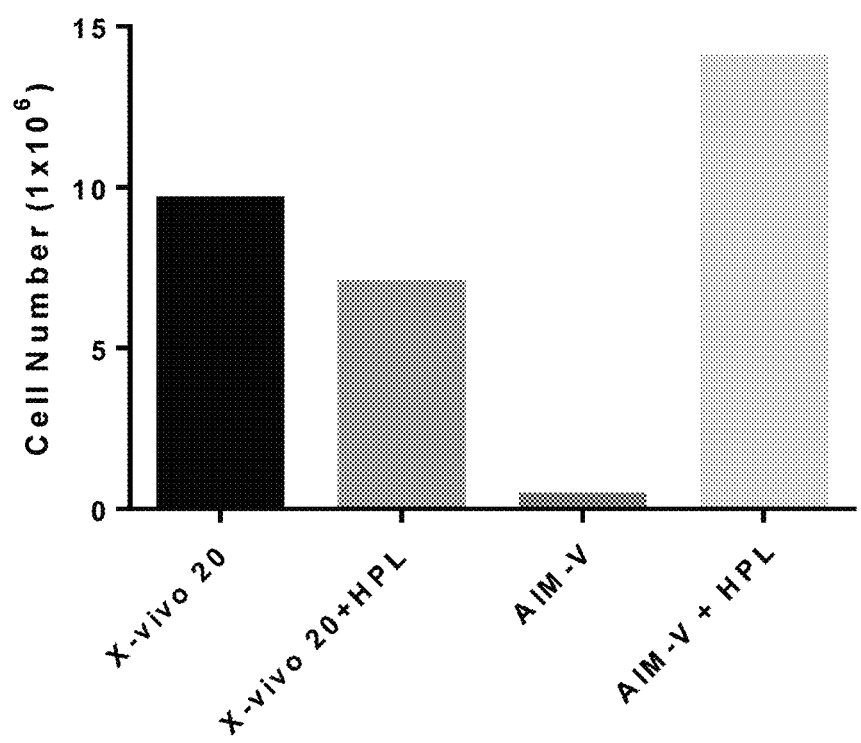
FIG. 1A illustrates cell numbers of the modified NK cells cultured with various culturing medium.

The foregoing and other aspects of the present disclosure will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process, or method.

The transitional phrase "consisting of" excludes any elements, steps, or ingredients not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

Where applicants have defined an invention or a portion thereof with an open-ended term such as "comprising," it should be readily understood that (unless otherwise stated) the description should be interpreted to also describe such an invention using the term "consisting of."

All numbers herein may be understood as modified by "about." As used herein, the term "about" is used to indicate that a value includes for example, the inherent variation of error for a measuring device, the method being employed to determine the value, or the variation that exists among the study subjects. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer to alternatives only or the alternatives are mutually exclusive, although the disclosure supports a definition that refers to only alternatives and "and/or."

"Subject" as used herein refers to animals, including, for example, a mammalian subject diagnosed with or suspected of having or developing cancer(s). In an embodiment, the term "subject" can refer to a vertebrate having cancer or to a vertebrate deemed to be in need of cancer treatment. Subjects include warm-blooded animals, such as mammals, such as a primate, and, more preferably, a human. Non-human primates are subjects as well. The term subject includes domesticated animals, such as cats, dogs, apes, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

"Administering" or "Administration" is referred to herein as providing a NK cell or a pharmaceutical composition of the present application to a subject. By way of example and not limitation, administration may be performed via parenteral, subcutaneous, intramuscular, intravenous, intra-articular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal. For example, injection may be performed by intravenous (i.v.) injection, sub-cutaneous (s.c.) injection, intradermal (i.d.) injection, intraperitoneal (i.p.) injection, or intramuscular (i.m.) injection. One or more such routes may be employed. Parenteral administration can be, for example, by bolus injection or by gradual perfusion over time. Alternatively, or concurrently, administration may be by the oral route.

The use of the terms "treating," or "treatment" is referred to herein as administration of a NK cell or a pharmaceutical composition to a subject with the purpose to cure, alleviate, relieve, remedy, prevent, or ameliorate a disorder, symptoms of the disorder, a disease state secondary to the disorder, or predisposition toward the disorder. The terms "inhibiting," "reducing," or "prevention," or any variation of these terms, when used in the claims and/or the specification includes any measurable decrease or complete inhibition to achieve a desired result.

"Cancer(s)" that may be treated by the NK cell or the pharmaceutical composition of the application include those classified by site include cancer of the oral cavity and pharynx (lip, tongue, salivary gland, floor of mouth, gum and other mouth, nasopharynx, tonsil, oropharynx, hypopharynx, other oral/pharynx); cancers of the digestive system (esophagus; stomach; small intestine; colon and rectum; anus, anal canal, and anorectum; liver; intrahepatic bile duct; gallbladder; other biliary; pancreas; retroperitoneum; peritoneum, omentum, and mesentery; other digestive); cancers of the respiratory system (nasal cavity, middle ear, and sinuses; larynx; lung and bronchus; pleura; trachea, mediastinum, and other respiratory); cancers of the mesothelioma; bones and joints; and soft tissue, including heart; skin cancers, including melanomas and other non-epithelial skin cancers; Kaposi's sarcoma and breast cancer; cancer of the female genital system (cervix uteri; corpus uteri; uterus, ovary; vagina; vulva; and other female genital); cancers of the male genital system (prostate gland; testis; penis; and other male genital); cancers of the urinary system (urinary bladder; kidney and renal pelvis; ureter; and other urinary); cancers of the eye and orbit; cancers of the brain and nervous system (brain; and other nervous system); cancers of the endocrine system (thyroid gland and other endocrine, including thymus); lymphomas (Hodgkin's disease and non-Hodgkin's lymphoma), multiple myeloma, and leukemias (lymphocytic leukemia; myeloid leukemia; monocytic leukemia; and other leukemias).

Other cancers, classified by histological type, that may be suitable targets for the therapeutic compositions according to the present application include, but are not limited to, neoplasm, malignant; Carcinoma, not otherwise specified (NOS); Carcinoma, undifferentiated, NOS; Giant and spindle cell carcinoma; Small cell carcinoma, NOS; Papillary carcinoma, NOS; Squamous cell carcinoma, NOS; Lymphoepithelial carcinoma; Basal cell carcinoma, NOS; Pilomatrix carcinoma; Transitional cell carcinoma, NOS; Papillary transitional cell carcinoma; Adenocarcinoma, NOS; Gastrinoma, malignant; Cholangiocarcinoma; Hepatocellular carcinoma, NOS; Combined hepatocellular carcinoma and cholangiocarcinoma; Trabecular adenocarcinoma; Adenoid cystic carcinoma; Adenocarcinoma in adenomatous polyp; Adenocarcinoma, familial polyposis coli; Solid carcinoma, NOS; Carcinoid tumor, malignant; Bronchioloalveolar adenocarcinoma; Papillary adenocarcinoma, NOS; Chromophobe carcinoma; Acidophil carcinoma; Oxyphilic adenocarcinoma; Basophil carcinoma; Clear cell adenocarcinoma, NOS; Granular cell carcinoma; Follicular adenocarcinoma, NOS; Papillary and follicular adenocarcinoma; Nonencapsulating sclerosing carcinoma; Adrenal cortical carcinoma; Endometroid carcinoma; Skin appendage carcinoma; Apocrine adenocarcinoma; Sebaceous adenocarcinoma; Ceruminous adenocarcinoma; Mucoepidermoid carcinoma; Cystadenocarcinoma, NOS; Papillary cystadenocarcinoma, NOS; Papillary serous cystadenocarcinoma; Mucinous cystadenocarcinoma, NOS; Mucinous adenocarcinoma; Signet ring cell carcinoma; Infiltrating duct carcinoma; Medullary carcinoma, NOS; Lobular carcinoma, NOS; Inflammatory carcinoma; Paget's disease, mammary; Acinar cell carcinoma; Adenosquamous carcinoma; Adenocarcinoma w/ squamous metaplasia; Thymoma, malignant; Ovarian stromal tumor, malignant; Thecoma, malignant; Granulosa cell tumor, malignant; Androblastoma, malignant; Sertoli cell carcinoma; Leydig cell tumor, malignant; Lipid cell tumor, malignant; Paraganglioma, malignant; Extra-mammary paraganglioma, malignant; Pheochromocytoma; Glomangiosarcoma; Malignant melanoma, NOS; Amelanotic melanoma; Superficial spreading melanoma; Malig melanoma in giant pigmented nevus; Epithelioid cell melanoma; Blue nevus, malignant; Sarcoma, NOS; Fibrosarcoma, NOS; Fibrous histiocytoma, malignant; Myxosarcoma; Liposarcoma, NOS; Leiomyosarcoma, NOS; Rhabdomyosarcoma, NOS; Embryonal rhabdomyosarcoma; Alveolar rhabdomyosarcoma; Stromal sarcoma, NOS; Mixed tumor, malignant, NOS; Mullerian mixed tumor; Nephroblastoma; Hepatoblastoma; Carcinosarcoma, NOS; Mesenchymoma, malignant; Brenner tumor, malignant; Phyllodes tumor, malignant; Synovial sarcoma, NOS; Mesothelioma, malignant; Dysgerminoma; Embryonal carcinoma, NOS; Teratoma, malignant, NOS; Struma ovarii, malignant; Choriocarcinoma; Mesonephroma, malignant; Hemangiosarcoma; Hemangioendothelioma, malignant; Kaposi's sarcoma; Hemangiopericytoma, malignant; Lymphangiosarcoma; Osteosarcoma, NOS; Juxtacortical osteosarcoma; Chondrosarcoma, NOS; Chondroblastoma, malignant; Mesenchymal chondrosarcoma; Giant cell tumor of bone; Ewing's sarcoma; Odontogenic tumor, malignant; Ameloblastic odontosarcoma; Ameloblastoma, malignant; Ameloblastic fibrosarcoma; Pinealoma, malignant; Chordoma; Glioma, malignant; Ependymoma, NOS; Astrocytoma, NOS; Protoplasmic astrocytoma; Fibrillary astrocytoma; Astroblastoma; Glioblastoma, NOS; Oligodendroglioma, NOS; Oligodendroblastoma; Primitive neuroectodermal; Cerebellar sarcoma, NOS; Ganglioneuroblastoma; Neuroblastoma, NOS; Retinoblastoma, NOS; Olfactory neurogenic tumor; Meningioma, malignant; Neurofibrosarcoma; Neurilemmoma, malignant; Granular cell tumor, malignant; Malignant lymphoma, NOS; Hodgkin's disease, NOS; Hodgkin's; paragranuloma, NOS; Malignant lymphoma, small lymphocytic; Malignant lymphoma, large cell, diffuse; Malignant lymphoma, follicular, NOS; Mycosis fungoides; Other specified non-Hodgkin's lymphomas; Malignant histiocytosis; Multiple myeloma; Mast cell sarcoma; Immunoproliferative small intestinal disease; Leukemia, NOS; Lymphoid leukemia, NOS; Plasma cell leukemia; Erythroleukemia; Lymphosarcoma cell leukemia; Myeloid leukemia, NOS; Basophilic leukemia; Eosinophilic leukemia; Monocytic leukemia, NOS; Mast cell leukemia; Megakaryoblastic leukemia; Myeloid sarcoma; and Hairy cell leukemia.

An "effective amount," as used herein, refers to a dose of the modified NK cells or pharmaceutical composition that is sufficient to reduce the symptoms and signs of cancer, which include, but are not limited to, weight loss, pain or tumor mass which is detectable, either clinically as a palpable mass or radiologically through various imaging means.

In certain embodiments, it is desired to limit, reduce, or ameliorate the size of tumor or cancer lesions. The routes of administration will vary, naturally, with the location and nature of the lesion or site to be targeted, and include, e.g., regional, parenteral, intravenous, intramuscular, and/or systemic administration and formulation. Direct injection or injection into the vasculature or the vessels to and from and within an organ or tissue is specifically contemplated for target areas. Local, regional, or systemic administration also may be appropriate.

In the disclosure herein, the expression level or surface density of the cell surface antigen using FACS/flow cytometry analysis are defined in Table 1. The interpretation for the various expression levels in Table 1 is an example of defining the expression level of the cell surface antigen. It should be noted that the flow cytometry signal level intensity varies with the following factors: the flow cytometry, the software and different batches of antibody used.

TABLE 1

| Symbol | Interpretation |
| --- | --- |
| − | Flow cytometry signal level intensity less than or equal to $10^0$ (i.e., 1) |
| + (Dim) | Flow cytometry signal level intensity between $10^0$ to $10^1$ |
| + | Flow cytometry signal level intensity between $10^1$ to $10^2$ |
| + (hi) | Flow cytometry signal level intensity greater than or equal to $10^2$ |

Unless otherwise defined, all technical and scientific terms used herein have the same meaning as commonly understood by one of ordinary skill in the art to which this invention belongs. All publications, patent applications, patents and other references cited herein are incorporated by reference in their entireties for the teachings relevant to the sentence and/or paragraph in which the reference is presented.

Modified NK Cells

Naturally occurring or conventional NK cells have $CD16^+CD56^+$ phenotype. In one embodiment, the naturally occurring or conventional NK cells have $CD3^-CD14^-CD19^-CD56^+CD16^+NKG2D^+CD11c^{dim}$ phenotype, as illustrated in Table 2.

In one embodiment, the present application provides a modified NK cell comprising a $CD3^-CD19^-CD14^-CD56^{hi}CD16^{dim}NKG2D^+CD11c^+CD86^+HLA\text{-}DR^+CD83^-$ cell phenotype, as illustrated in Table 2. The modified NK cell of the present application is non-naturally occurring. The modified NK cells comprise one or more of the fully activated dendritic (DC) cell surface antigens (for example, HLA-DR and CD86) and possess both NK cell function and DC cell function and an enhanced anti-cancer activity.

TABLE 2

Phenotypic comparison of conventional NK cells and modified NK cells

|  | Conventional NK | Modified NK |
| --- | --- | --- |
| CD3 | − | − |
| CD14 | − | − |
| CD19 | − | − |
| CD56 | + | hi |
| CD16 | + | dim |
| NKG2D | + | + |
| CD11c | dim | + |
| HLA-DR | − | + |
| CD86 | − | + |
| CD83 | − | − |

Specifically, the present application provides a modified NK cell comprising a $CD16^{dim}CD56^{hi}$ phenotype, wherein said $CD16^{dim}CD56^{hi}$ NK cell does not comprise a CD83 cell surface antigen (having a phenotype of $CD16^{dim}CD56^{hi}CD83^-$).

WO2015/100495 disclosed a modified NK cell comprising a $CD3^-CD19^-CD14^-CD56^+CD16^+NKG2D^+CD11c^-CD86^+HLA\text{-}DR^+CD83^+$ phenotype. Comparing to the modified NK cell of WO2015/100495, the modified NK cell of the present application has a general DC cell surface antigen CD11c but lacks a fully activated DC cell surface antigen CD83. Regardless, the modified NK cell of the present application possess higher and stronger DC cell function, e.g. antigen presentation, than the modified NK cell of WO2015/100495 by 66%.

In one embodiment, the expression level or surface density of the cell surface antigen is quantified by exposing the modified NK cells to a fluorescent dye-tagged specific anti-human monoclonal antibody (e.g., CD86-PE (Beckman Coulter; Cat. No: IM2729U) or Anti-human CD83-PE-Cy5 (BioLegend; Cat. No: 305310), followed by sorting of the modified NK cells using flow cytometer (e.g. Navios, commercially available from Beckman Coulter, Inc., USA).

The modified NK cells can be generated from a single individual, e.g. autologous or allogeneic.

Pharmaceutical Composition

In one embodiment, the present application provides pharmaceutical compositions comprising a modified NK cell described herein, and a pharmaceutically acceptable carrier or excipient.

The present application also provides methods of inhibiting cancer cells by administering to a subject in need thereof the present modified NK cells or the present pharmaceutical composition in an amount effective to inhibit cancer cells. Without being bound by any particular theory, it is believed that the modified NK cells inhibit cancer cells by one or more of the NK cell/DC cell functions: enhancing cytotoxicity, stimulating cancer-specific T lymphocyte proliferation or IFN-γ secretion.

Routes of administration of the present pharmaceutical compositions or modified NK cells include, but are not limited to, intravenous, intramuscular, subcutaneous, oral, topical, intradermal, transdermal, subdermal, parenteral, rectal, spinal, or epidermal administration. In one embodiment, the modified NK cells are administered by intravenous injection or infusion.

The pharmaceutical compositions of the present application can be prepared as injectables, either as liquid solutions or suspensions, or as solid forms which are suitable for solution or suspension in liquid vehicles prior to injection.

The present modified NK cells are formulated into pharmaceutical compositions for delivery to a mammalian subject. The pharmaceutical composition is administered alone, and/or mixed with a pharmaceutically acceptable vehicle, excipient or carrier. Suitable vehicles are, for example, saline (e.g. normal saline), dextrose, glycerol, platelet-rich plasma (PRP), or the like, and combinations thereof. In addition, the vehicle can contain minor amounts of auxiliary substances such as wetting or emulsifying agents, pH buffering agents, or adjuvants. Pharmaceutically acceptable carriers can contain a physiologically acceptable compound that acts to, e.g., stabilize, or increase or decrease the absorption or clearance rates of the pharmaceutical compositions of the present application. Physiologically acceptable compounds can include, e.g., carbohydrates, such as glucose, sucrose, or dextran, antioxidants, such as ascorbic acid or glutathione, chelating agents, low molecular weight proteins, detergents, liposomal carriers, or excipients or other stabilizers and/or buffers. Other physiologically acceptable compounds include wetting agents, emulsifying agents, dispersing agents or preservatives. See e.g., the 21st edition of Remington's Pharmaceutical Science, Mack Publishing Company, Easton, Pa. ("Remington's"). The pharmaceutical compositions of the present application can also include ancillary substances, such as pharmacological agents, cytokines, or other biological response modifiers.

Actual methods of preparing such dosage forms are known, or will be apparent, to those skilled in the art. See, e.g., Remington's Pharmaceutical Sciences, Mack Publishing Company, Easton, Pa., 21st edition.

The modified NK cells or the present pharmaceutical compositions can be administered in a single dose treatment or in multiple dose treatments on a schedule and over a time period appropriate to the age, weight and condition of the subject, the particular composition used, and the route of administration, whether the modified NK cells or the present pharmaceutical composition is used for prophylactic or curative purposes, etc. For example, in one embodiment, the modified NK cells or pharmaceutical composition according to the present application is administered once per month, twice per month, three times per month, every other week (qow), once per week (qw), twice per week (biw), three times per week (tiw), four times per week (qiw), five times per week, six times per week, every other day (qod), daily (qd), twice a day (bid), three times a day (tid) or four times a day (qid).

The duration of treatment of the modified NK cells or the pharmaceutical composition according to the present application, e.g., the period of time over which the modified NK cell or pharmaceutical composition is administered, can vary, depending on any of a variety of factors, e.g., subject response, etc. For example, the modified NK cells or pharmaceutical composition can be administered over a period of time ranging from about one or more seconds to one or more minutes, one or more hours to one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

It is advantageous to formulate parenteral pharmaceutical compositions or modified NK cells in dosage unit form for ease of administration and uniformity of dosage. Dosage unit form as used herein refers to physically discrete units suited as unitary dosages for the subject to be treated; each unit containing a predetermined quantity of modified NK cells calculated to produce the desired therapeutic effect in association with the required pharmaceutical carrier.

The data obtained from the cell culture assays and animal studies can be used in formulating a range of dosage for use in humans. In one embodiment, the dosage of such NK cells lies within a range of circulating concentrations that include the $ED_{50}$ with little or no toxicity. The dosage can vary within this range depending upon the dosage form employed and the route of administration utilized. In another embodiment, the therapeutically effective dose can be estimated initially from cell culture assays. A dose can be formulated in animal models to achieve a circulating plasma concentration range that includes the $IC_{50}$ (i.e., the concentration of the modified NK cells which achieves a half-maximal inhibition of symptoms) as determined in cell culture. Sonderstrup, Springer, Sem. Immunopathol. 25: 35-45, 2003. Nikula et al, Inhal. Toxicol. 4(12j: 123-53, 2000.

The pharmaceutical composition is formulated to contain an effective amount of the present modified NK cells, wherein the amount depends on the animal to be treated and the condition to be treated. The specific dose level for any particular subject depends upon a variety of factors including the activity of the specific modified NK cells, the age, body weight, general health, sex, diet, time of administration, route of administration, and rate of excretion, drug combination and the severity of the particular disease undergoing therapy. An exemplary, non-limiting range for a therapeutically or prophylactically effective amount of the modified NK cells of the present application is at least about $1\times10^3$ cells per dose to about $1\times10^9$ cells per dose. Other dosages are also possible, including, but not limited to, $1\times10^4$, $1\times10^5$, $1\times10^6$, $1\times10^7$, $1\times10^8$ or $1\times10^9$ cells per dose.

The modified NK cells or the pharmaceutical composition can be administered alone or in combination with another therapeutic agent, e.g., chemotherapy, radiotherapy or targeted therapy or cancer vaccine.

Methods of Identifying and Culturing the Modified NK Cells

Figure 7:
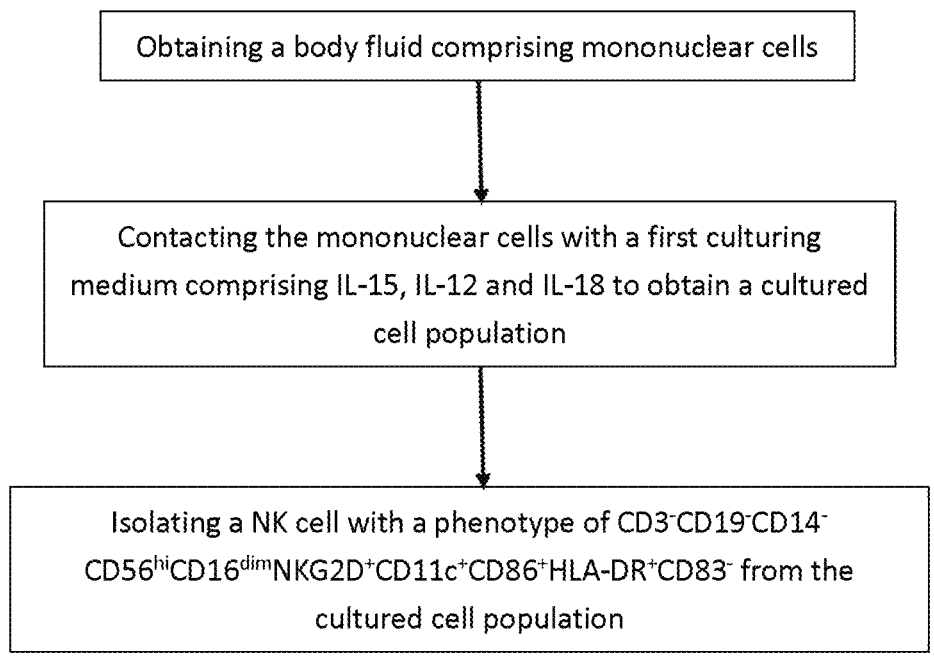
FIG. 7 is a flow chart in accordance with an embodiment of the method of culturing a modified NK cell.

In one embodiment, the methods of identifying the initial NK cells and culturing the modified NK cells are illustrated as in FIG. 7. Briefly, the method comprises at least the steps of: obtaining a body fluid containing mononuclear cells; contacting the mononuclear cells with a first culturing medium comprising IL-15, IL-12 and IL-18 to obtain a cultured cell population; and isolating a NK cell possessing both NK cell function and dendritic cell function from the cultured cell population with a cell marker $CD3^-CD19^-CD14^-CD56^{hi}CD16^{dim}NKG2D^+CD11c^+CD86^+HLA-DR^+CD83^-$.

Preferably, the mononuclear cells used herein for the selection or production of the modified NK cells are purified $CD3^-CD14^-CD19^-$ mononuclear cells as the initial cell population for the expansion culture.

In one embodiment, the identification/depletion steps to obtain a highly purified fraction of $CD3^-CD14^-CD19^-$ mononuclear cells are as follows:
 (a) Collecting a sample from a subject. The sample includes, but is not limited to, any body fluids containing one or more mononuclear cells, such as peripheral blood, cord blood or bone marrow sample.
 (b) Separating the mononuclear cells within the sample in step (a) from other types of blood cells via centrifugation (Ficoll-Paque™ PREMIUM, GE Healthcare USA). Other methods of separating mononuclear cells are known, or will be apparent, to those skilled in the art.
 (c) Depleting one or more mononuclear cells comprising CD3 cell surface antigen (for example, mononuclear cells phenotypes $CD3^+CD56^-$ and $CD3^+CD56^+$), CD14 cell surface antigen or CD19 cell surface antigen from the other mononuclear cells in step (b), for example, by MACS sorting (Mitenyi Biotec, Germany).
 (d) Collecting the $CD3^-CD14^-CD19^-$ mononuclear cells in step (c) for culture. One embodiment of the disclosure provides methods for identifying an initial cell from a sample, comprising depleting one or more of the following cell surface antigens from a mononuclear cell in said sample: CD3, CD14, or CD19, wherein said initial cell is substantially free of one or more of the cell surface antigens selected from CD3, CD14, and CD19.

In one embodiment, the mononuclear cells comprising CD3 in Step (b) are depleted in the sample. In another embodiment, the mononuclear cells comprising CD14 in Step (b) are depleted in the sample. In yet another embodiment, the mononuclear cells comprising CD19 in Step (b) are depleted in the sample. In yet another embodiment, one or more mononuclear cells comprising CD14 and one or more mononuclear cells comprising CD3 in Step (b) are depleted in the sample. In yet another embodiment, one or more mononuclear cells comprising CD14 and one or more mononuclear cells comprising CD19 in Step (b) are depleted in the sample. In yet another embodiment, one or more mononuclear cells comprising CD19 and one or more mononuclear cells comprising CD3 in Step (b) are depleted in the sample. In yet another embodiment, one or more mononuclear cells comprising CD19, one or more mononuclear cells comprising CD3 and one or more mononuclear cells comprising CD14 in Step (b) are depleted in the sample.

In one embodiment, substantially all of the mononuclear cells comprising CD3 are depleted in the sample. In another embodiment, substantially all of the mononuclear cells comprising CD14 are depleted in the sample. In yet another embodiment, substantially all of the mononuclear cells comprising CD19 are depleted in said sample.

In one embodiment, the composition for culturing the cells further includes IFN-γ. In alternative embodiment, the composition for culturing the cells includes no IFN-γ. In this embodiment, IFN-γ shed little effect on the generation of the modified NK cells disclosed herein.

The culturing time of the composition comprising IL-12 may be critical for function of the modified NK cells. In an embodiment, mononuclear cells may be cultured with IL-12, e.g. human IL-12, for 1 to 12 days, preferably 1, 2, 3, 4, 5, 6, 7, 8, 9, 10, 11, or 12 days, to generate the modified NK cells. In an embodiment, mononuclear cells cultured with IL-12 for 3, 6, 9 or 12 days generate modified NK cells with similar cell yields and phenotypic patterns. In another embodiment, prolong exposure of IL-12, e.g. 12 days, augmented cytotoxicity and antigen-presenting cell activities of the cultured cells as compared to the cells with IL-12 exposure for less time, e.g. 9 days.

In one embodiment, the composition for culturing the cells further includes IL-18. In one embodiment, the effective concentration of IL-18 is about 1 to 300 ng/mL, such as, for example, 50, 100, 150, 200, 250, 300 ng/mL. In another embodiment, the effective concentration of IL-18 is about 10 to about 250 ng/mL, or any value or range of values there between in 10 ng/mL increments (e.g., about 30 ng/mL, about 220 ng/mL, etc.).

In another embodiment, IL-18 shed effect on the phenotypic patterns and the functional activities of the modified NK cells. Long term IL-18 exposure may have the opposite effects on cell size, phenotype and functional activities. In an embodiment, mononuclear cells may be cultured with IL-18, e.g. human IL-18, for 1 to 12 days, preferably 1, 2, 3, 4, 5, 6, 7, 8, 9, 10, 11, or 12 days, to generate the modified NK cells. In an embodiment, mononuclear cells cultured with IL-18 for 3, 6, 9 or 12 days generate modified NK cells with various phenotypes. In another embodiment, adequate exposure of IL-18, e.g. 6 days, may have opposite effects on cell size, phenotype and function of the modified NK cells as compared to the cells with IL-18 exposure for less time, e.g. 6 days.

In one embodiment, a highly purified fraction of CD3$^-$CD14$^-$CD19$^-$ mononuclear cells are in contact with a culture composition comprising IL-18, IL-15 and/or IL-12. In another embodiment, the CD3$^-$CD14$^-$CD19$^-$ mononuclear cells in step (c) are mixed with a composition substantially consisting of hematopoietic cell medium (e.g. X-vivo 20), IL-18, IL-15, IL-12 and serum protein (e.g. human platelet lysate). In still another embodiment, the CD3$^-$CD14$^-$CD19$^-$ mononuclear cells in step (c) are mixed with a composition substantially consisting of X-vivo 20, IL-18, IL-15, IL-12 and human platelet lysate.

In another embodiment, the composition further comprises a hematopoietic cell medium. Non limiting example of the hematopoietic cell medium includes X-vivo 10, X-vivo 15, X-vivo 20 (commercially available from Lonza, Switzerland) and AIM-V (commercially available from ThermoFisher Scientific, United States).

In yet another embodiment, the composition further comprises serum protein, e.g. human platelet lysate. In the present application, "serum protein" are the proteins present in blood or plasma that serve many different functions, including transport and regulation of a cellular activity. Non limiting example of the serum protein includes enzymes, complement components, protease inhibitors, kinin precursors, serum albumin, globulins, and fibrinogen etc.

Non limiting example of the composition for culturing the cells includes (a) hematopoietic cell medium+IL-15+IL-18; (b) hematopoietic cell medium+IL-12+IL-18; (c) hematopoietic cell medium+IL-15+IL-12+IL-18; (d) X-vivo 20+IL-15+IL-18; (e) X-vivo 20+IL-12+IL-18; (f) X-vivo 20+IL-15+IL-12+IL-18; (g) AIM-V+IL-15+IL-18; (h) AIM-V+IL-12+IL-18; (i) AIM-V+IL-15+IL-12+IL-18; (j) hematopoietic cell medium+IL-15+IL-18+serum protein; (k) hematopoietic cell medium+IL-12+IL-18+serum protein; (l) hematopoietic cell medium+IL-15+IL-12+IL-18+serum protein; (m) X-vivo 20+IL-15+IL-18+serum protein; (n) X-vivo 20+IL-12+IL-18+serum protein; (o) X-vivo 20+IL-15+IL-12+IL-18+serum protein; (p) AIM-V+IL-15+IL-18+serum protein; (q) AIM-V+IL-12+IL-18+serum protein; and (r) AIM-V+IL-15+IL-12+IL-18+serum protein.

In one embodiment, the composition is used for culture the modified NK cells, in the presence of 5% $CO_2$ at 37° C.

The composition according to some embodiments of the application enhances the proliferation of the modified NK cells. In one embodiment, the composition substantially enhance the expression of CD11c cell surface antigens on the modified NK cells. In another embodiment, the composition enhances the expression of fully activated DC cell markers such as HLA-DR and CD86 cell surface antigens but not CD83 cell surface antigens on the modified NK cells. Proliferation rate of the modified NK cells was determined by the purity of CD3$^-$CD14$^-$CD19$^-$ cells via FACS and viable counts. Other assays for cell proliferation are well known in the art, e.g., clonogenic assays, metabolic assays, and direct proliferation assays.

An exemplary non-limiting range for the contact time of the CD3$^-$CD14$^-$CD19$^-$ mononuclear cells and the composition is from about 1 minute to about 1 hour, from about 1 hour to about 24 hours, from about 1 day to about 3 days, from about 1 day to about 6 days, from about 1 day to about 9 days, from about 1 day to about 12 days, from about 3 days to about 6 days, from about 3 days to about 9 days, from about 3 days to about 12 days, from about 6 days to about 9 days, from about 6 days to about 12 days, or at least 1 day. In one embodiment, the contact time is about 3 days. In another embodiment, the contact time is about 6 days.

In one embodiment, the CD3$^-$CD14$^-$CD19$^-$ mononuclear cells are in contact with a first composition comprising an IL-15, an IL-12 and an IL-18; followed by contacting with a second composition comprising an IL-15 and an IL-12. In another embodiment, the first and second compositions further comprise a hematopoietic cell medium, such as AIM-V or X-vivo, and/or a serum protein, such as human platelet lysate.

The following examples of specific aspects for carrying out the present invention are offered for illustrative purposes only, and are not intended to limit the scope of the present invention in any way.

EXAMPLES

Example 1: Selection of Culture Medium $CD3^-CD14^-CD19^-$ mononuclear cells were cultured in AIM-V medium or X-vivo 20 medium in the presence of 30 ng/mL human recombinant IL-15 (hIL-15), 3 ng/mL human recombinant IL-12 (hIL-12), 60 ng/mL human recombinant IL-2 (hIL-2), 37.5 ng/mL human recombinant IL-18 (hIL-18) and optionally 4% (w/w) human platelet lysate (HPL) for 15 days. Cell numbers in each group were counted by using trypan blue dye exclusion. Furthermore, the cells were subsequently stained with monoclonal antibodies (mAbs) of NKG2D-PE, CD45-ECD, CD16-PE-Cy7, CD56-APC-Alexa Flour 700, CD3-APC-Alexa Flour 750, CD14-APC-Alexa Flour 750, CD19-APC-Alexa Flour 750 (Beckman Coulter), CD86-Alexa488, CD83-PE-Cy5, CD11c-APC, and HLA-ABC-Pacific Blue (Biolegend). Samples were acquired and analyzed via Navios Flow Cytometer while the data analysis was done via Kaluza software (Beckman Coulter).

Figure 1B:
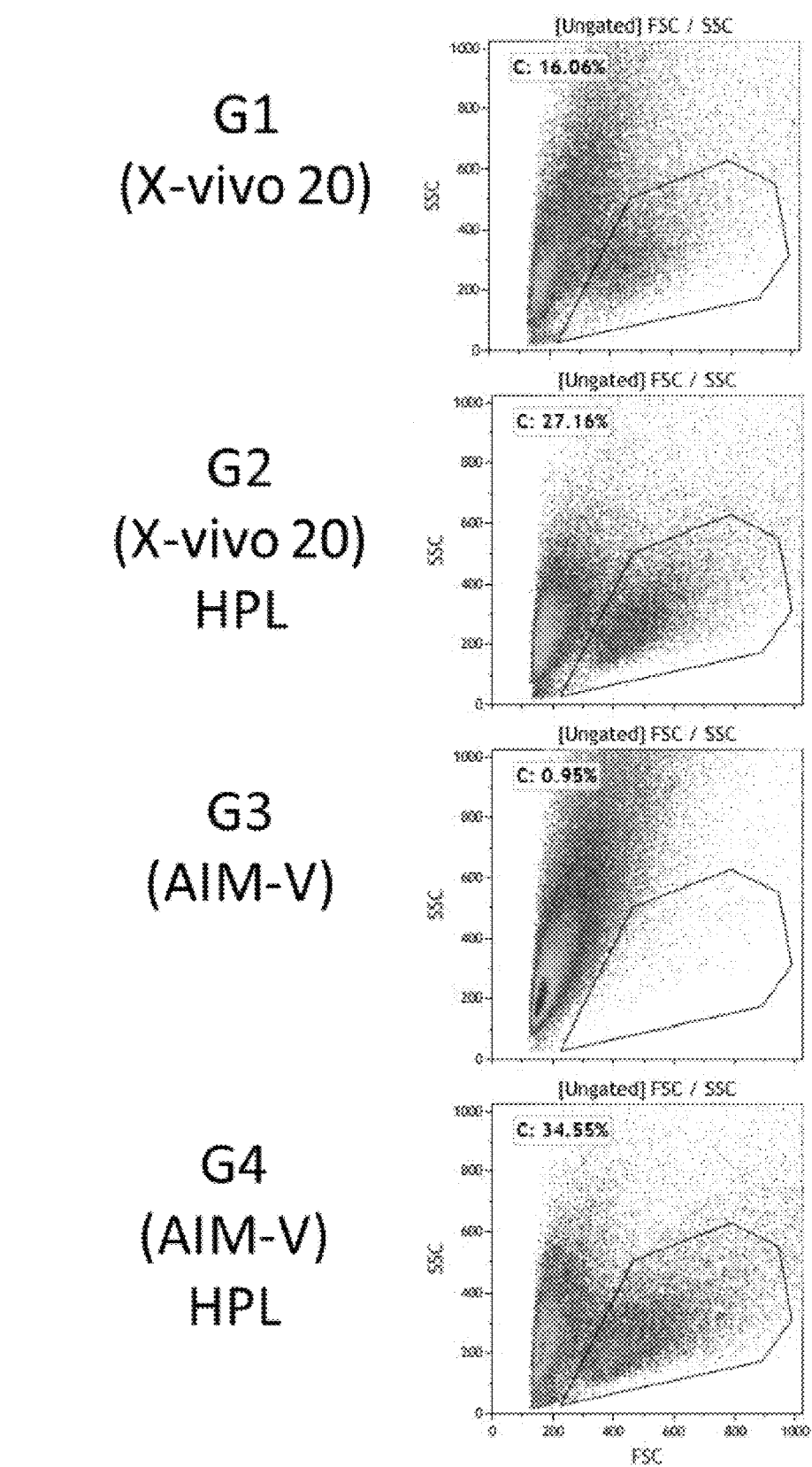
FIGS. 1B and 1C illustrate an assembly of flow cytometry images of the modified NK cells cultured with various culturing medium for expression of NKG2D, CD45, CD16, CD56, CD3, CD14, CD19, CD86, CD83, CD11c, and HLA-ABC.
Figure 1B:
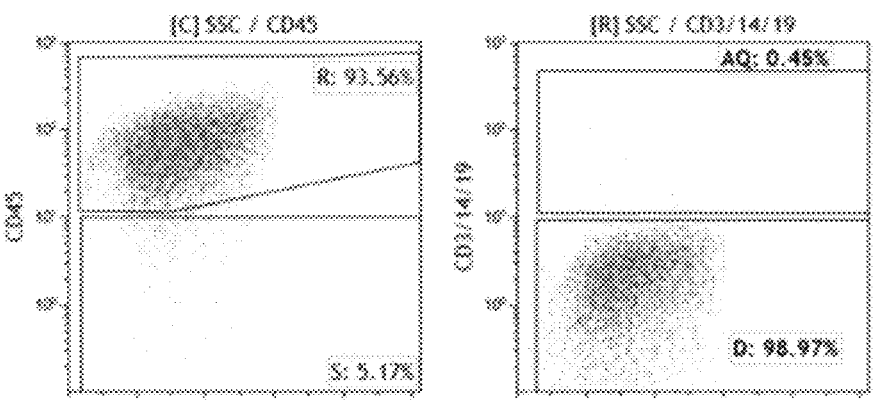
Figure 1B:
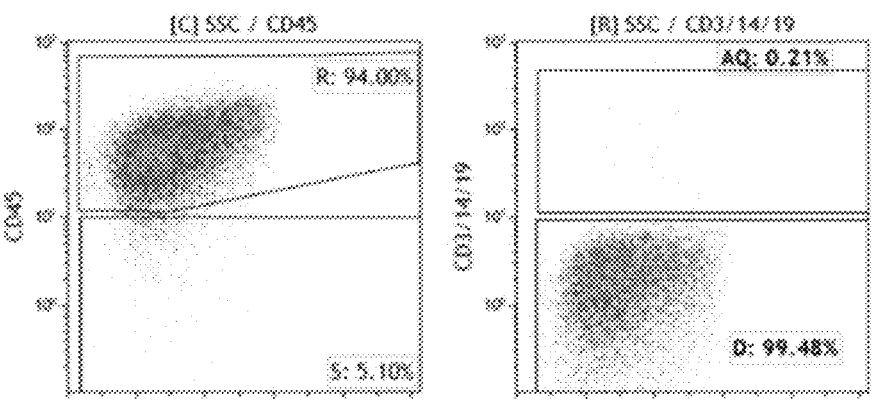
Figure 1B:
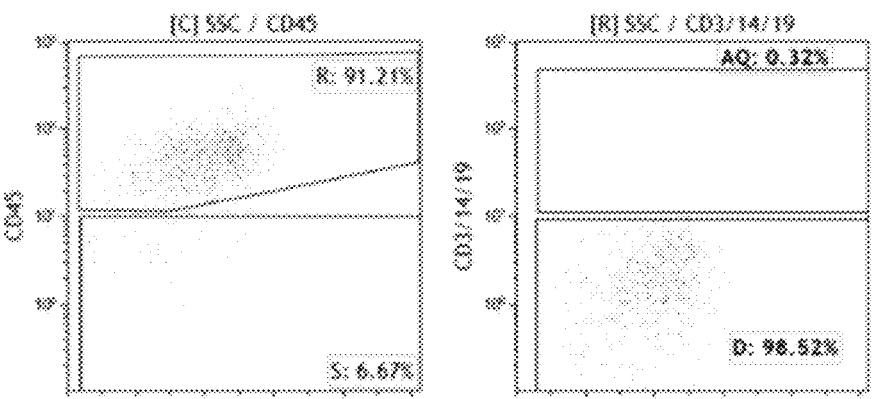
Figure 1B:
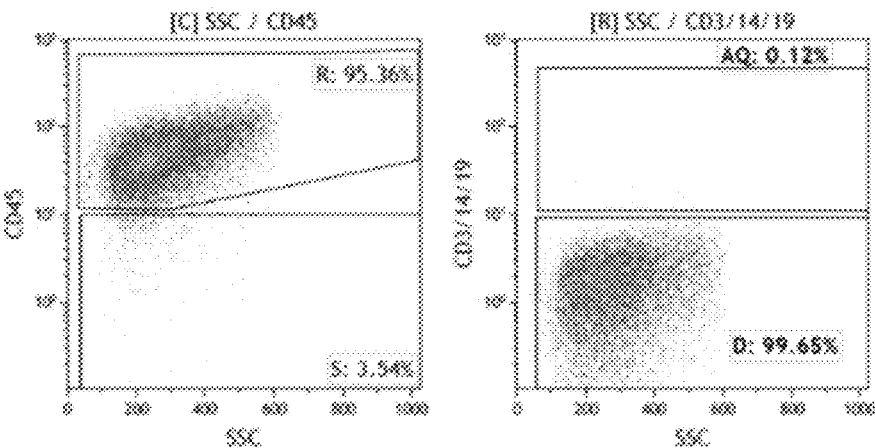
Figure 1B:
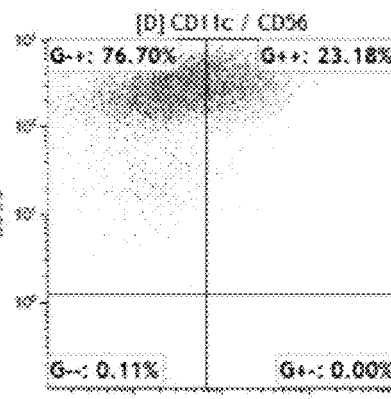
Figure 1B:
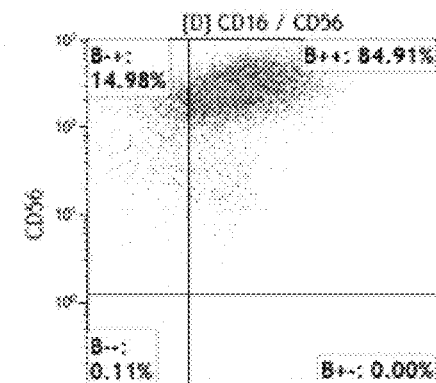
Figure 1B:
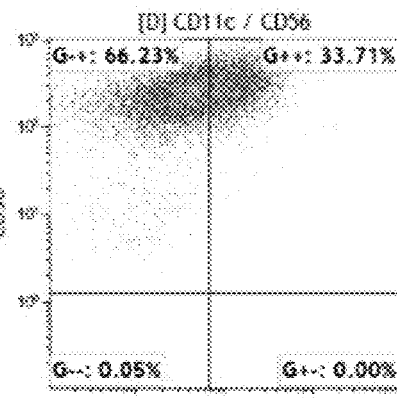
Figure 1B:
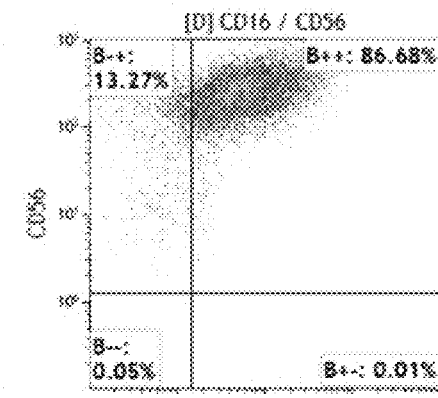
Figure 1B:
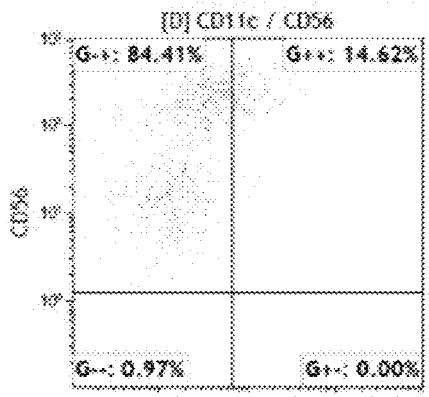
Figure 1B:
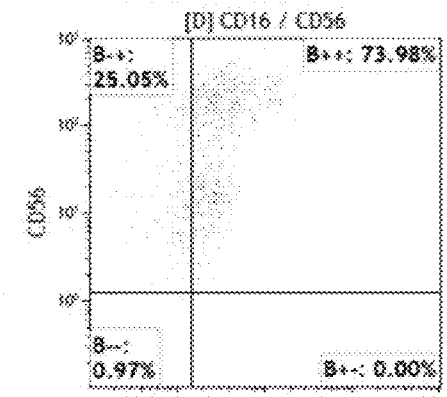
Figure 1B:
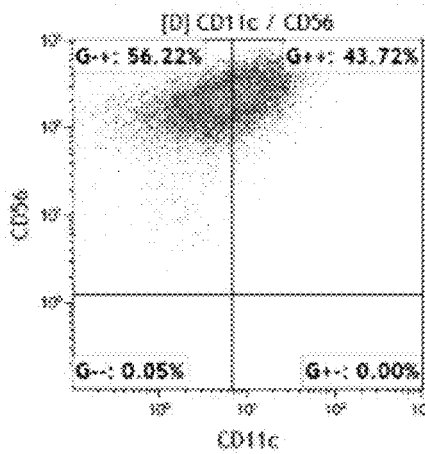
Figure 1B:
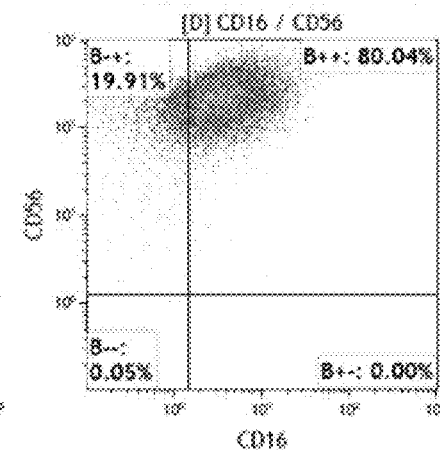
Figure 1C:
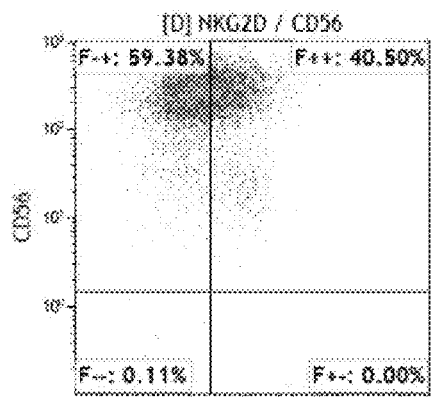
Figure 1C:
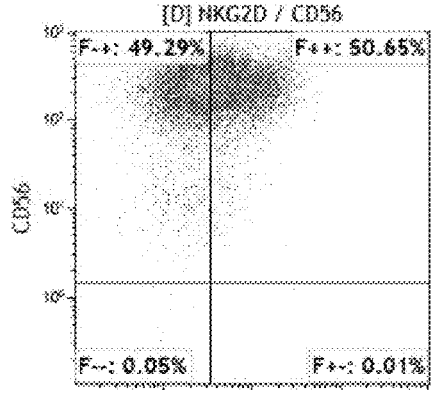
Figure 1C:
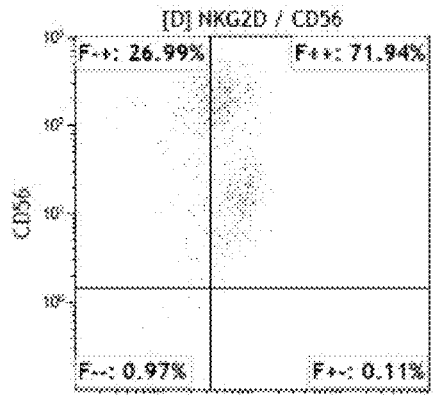
Figure 1C:
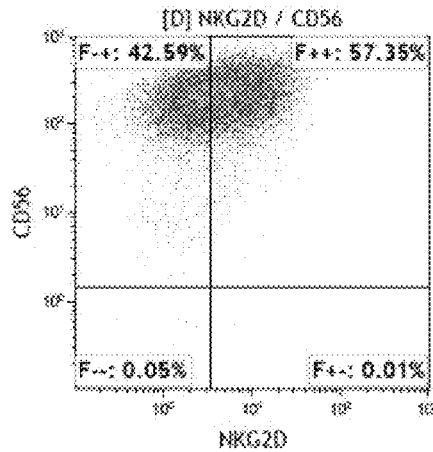
Figure 1C:
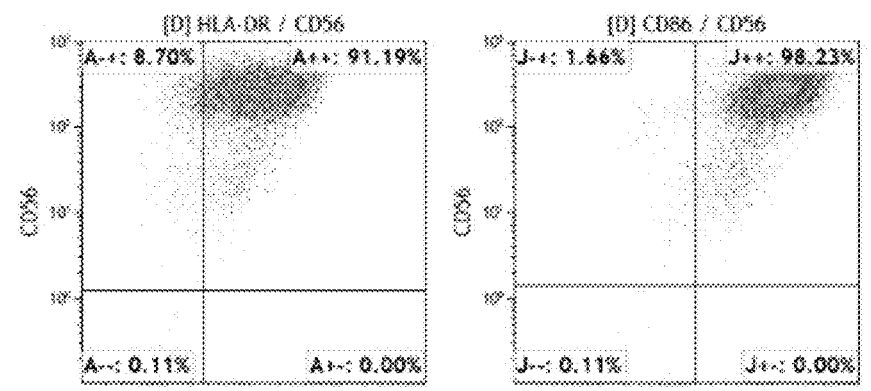
Figure 1C:
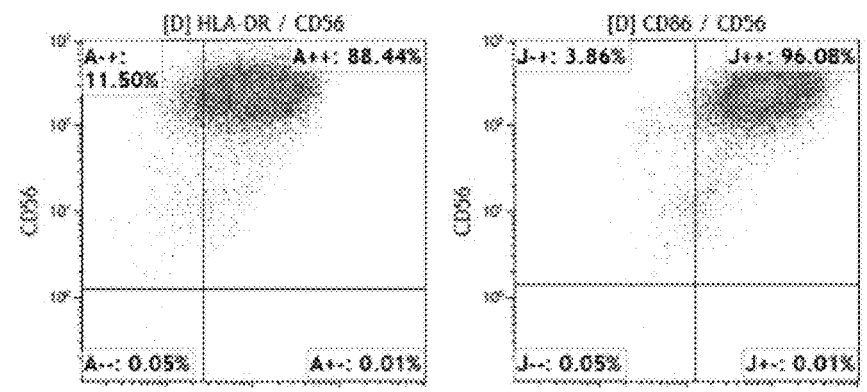
Figure 1C:
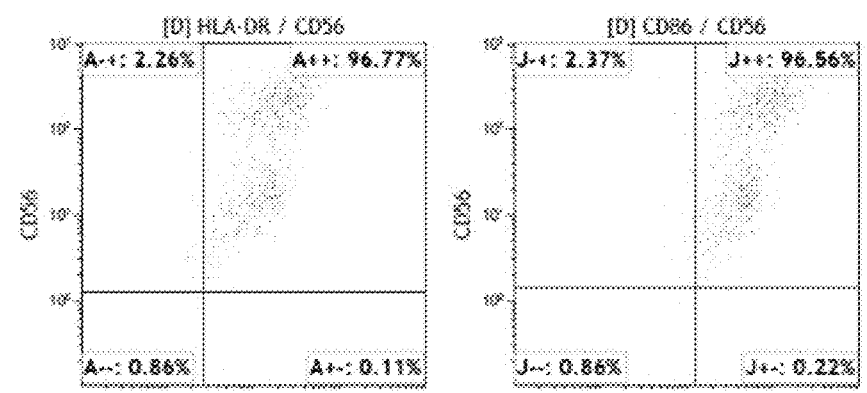
Figure 1C:
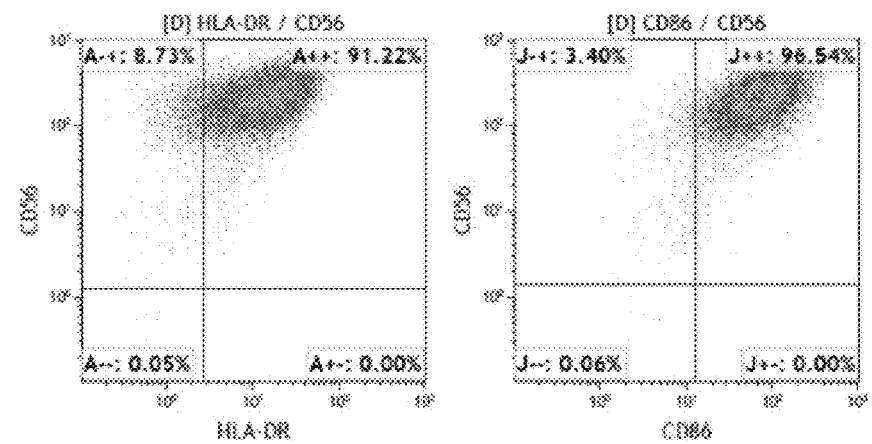
Figure 1C:
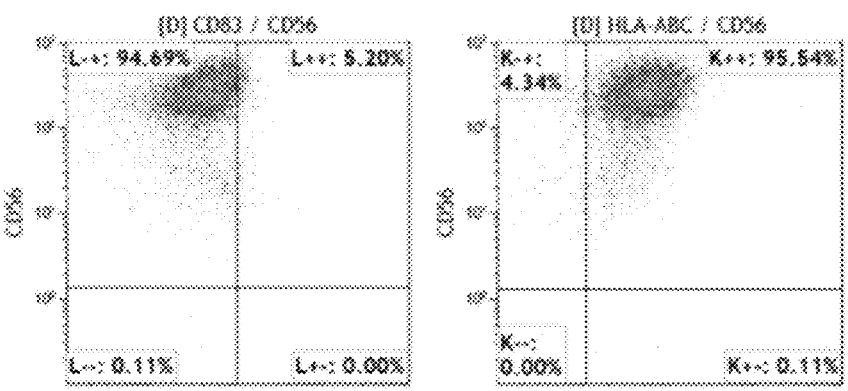
Figure 1C:
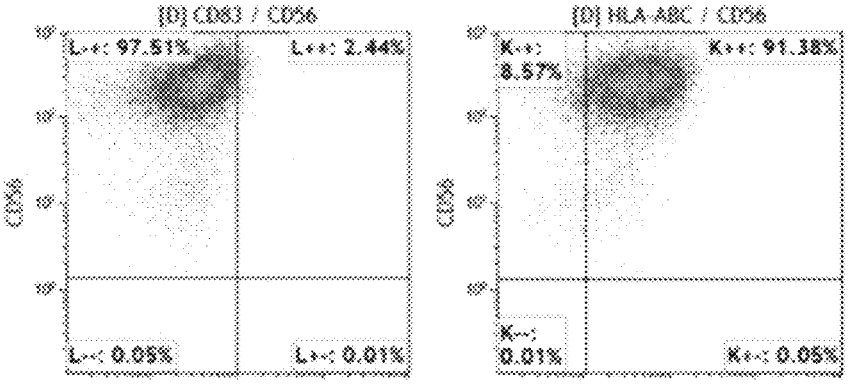
Figure 1C:
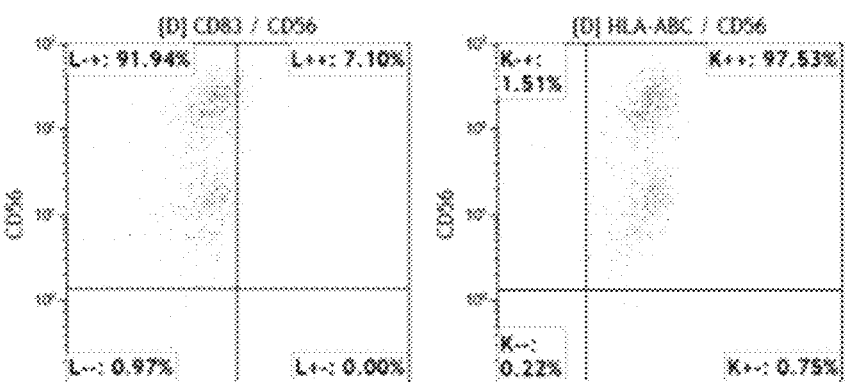
Figure 1C:
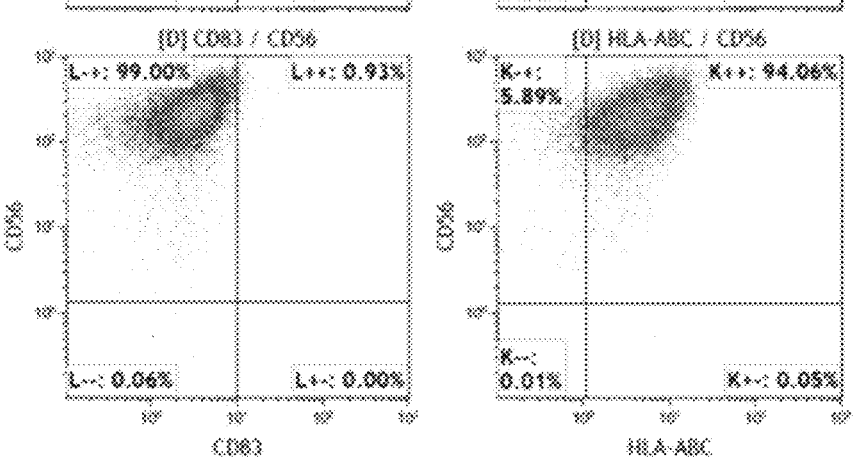

As shown in FIG. 1A, the cell number of the cell cultured in AIM-V medium supplemented with HPL reached better yields of the cell culture than those by X-vivo 20, indicating that AIM-V medium with HPL had the potential to increase the yield of cells. In addition, culturing the cells with AIM-V medium supplemented with HPL results in comparable phenotypes as those by X-vivo 20 (FIGS. 1B-1C).

Example 2: Selection of the Initial Mononuclear Cells $CD3^-CD14^-CD19^-$ (TN1) or $CD25^-CD14^-CD19^-$ (TN2) mononuclear cells were cultured in AIM-V medium in the presence of 30 ng/mL hIL-15, 3 ng/mL hIL-12, 45 ng/mL human recombinant IFN-γ (hIFN-γ), and 4% (w/w) HPL for 9 days. The cultured cells were counted by using trypan blue dye exclusion and stained with mAbs of CD45-ECD, CD3-APC-Alexa Flour 750, CD14-APC-Alexa Flour 750, and CD19-APC-Alexa Flour 750 (Beckman Coulter). Samples were acquired and analyzed via Navios Flow Cytometer while the data analysis was done via Kaluza software (Beckman Coulter).

Figure 2A:
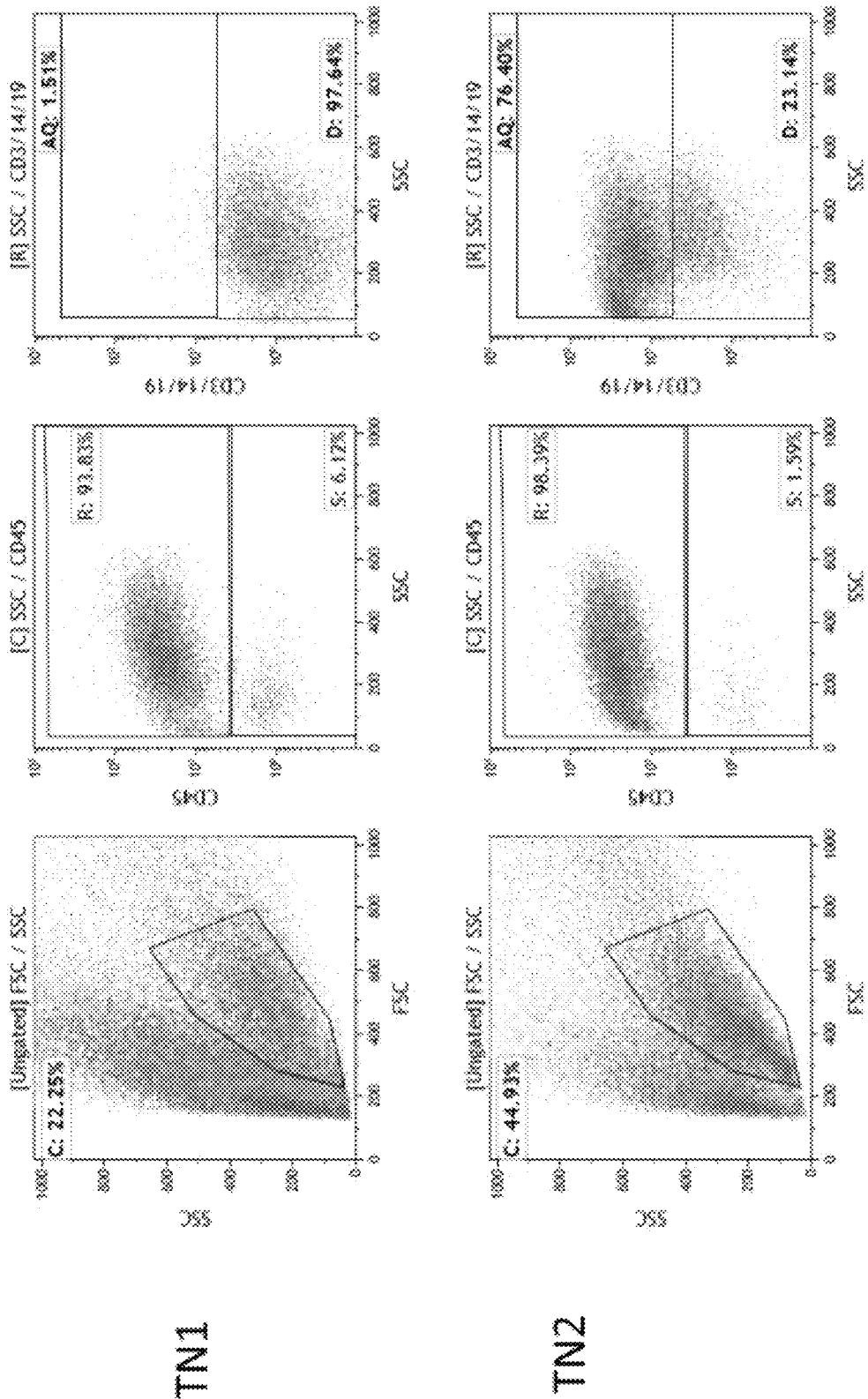
FIG. 2A illustrates an assembly of flow cytometry images of the modified NK cells cultured from various initial cells for expression of CD45, CD3, CD14, and CD19.

As shown in FIG. 2A and Table 3, the TN1 initial cells gave target cells with highly purity with better yields than those using TN2 initial cells.

TABLE 3

| Cells | Purity | Yields (cells) |
|---|---|---|
| TN1 | 91.62% | $1.22 \times 10^7$ |
| TN2 | 22.88% | $6.2 \times 10^6$ |

On the other hands, the cultured cells were stained with mAbs of NKG2D-PE, CD45-ECD, CD16-PE-Cy7, CD56-APC-Alexa Flour 700, CD3-APC-Alexa Flour 750, CD14-APC-Alexa Flour 750, CD19-APC-Alexa Flour 750 (Beckman Coulter), CD86-Alexa488, CD83-PE-Cy5, CD11c-APC, and HLA-ABC-Pacific Blue (Biolegend) to analyze their phenotypes. Samples were acquired and analyzed via Navios Flow Cytometer while the data analysis was done via Kaluza software (Beckman Coulter).

Figure 2B:
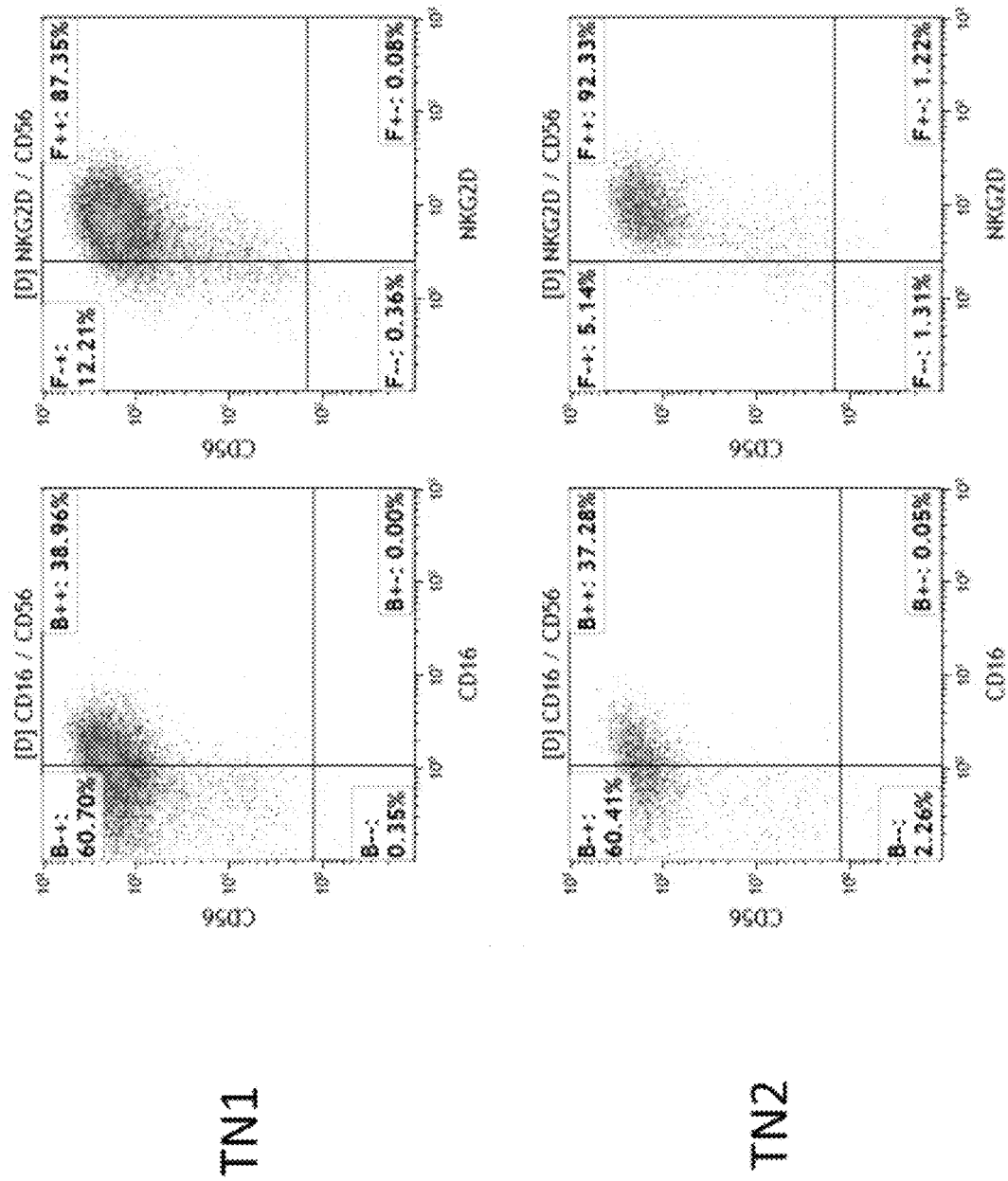
FIGS. 2B and 2C illustrate an assembly of flow cytometry images of the modified NK cells cultured from various initial cells for NK phenotypes and DC phenotypes, respectively.
Figure 2C:
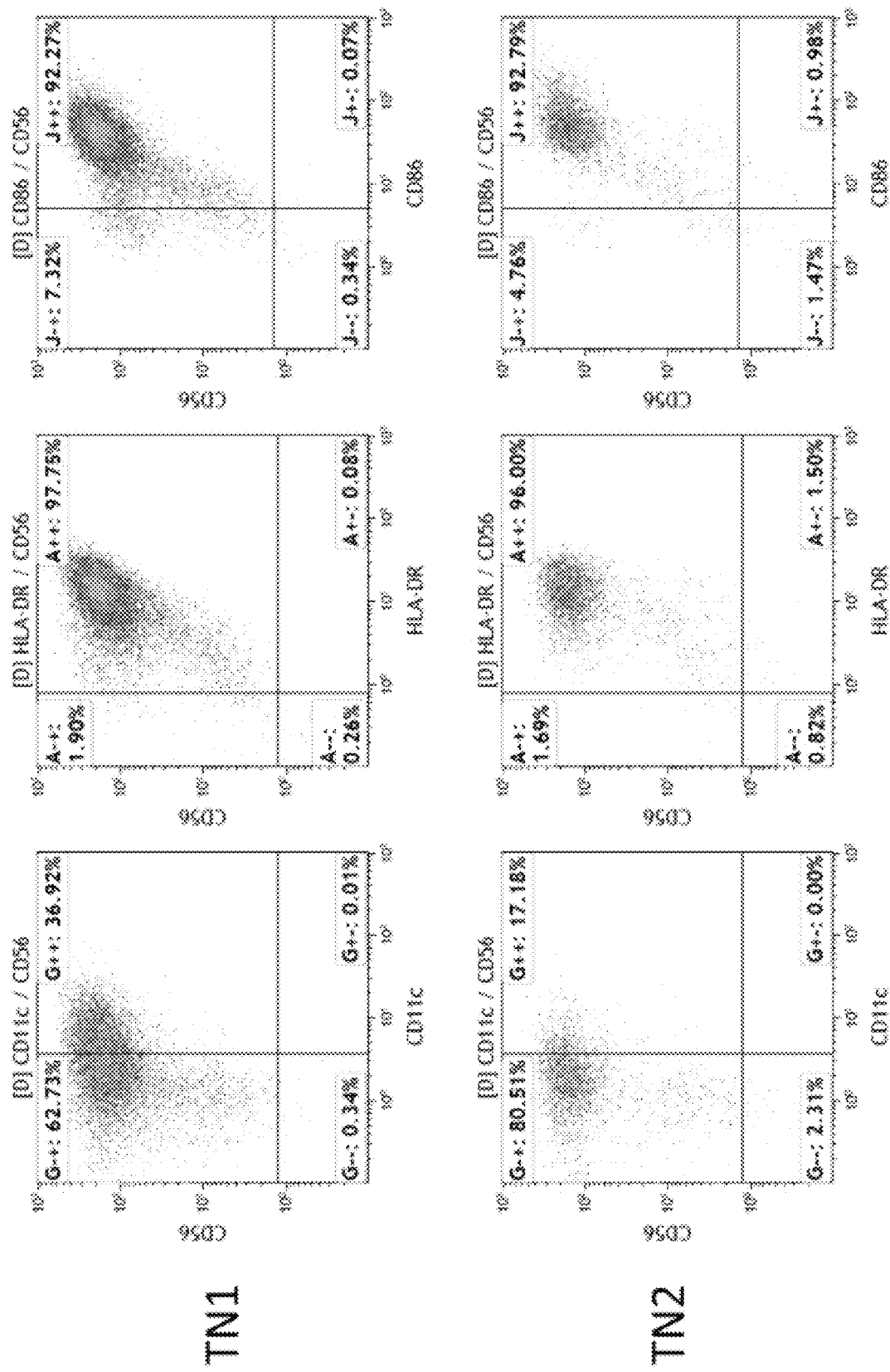
Figure 2C:
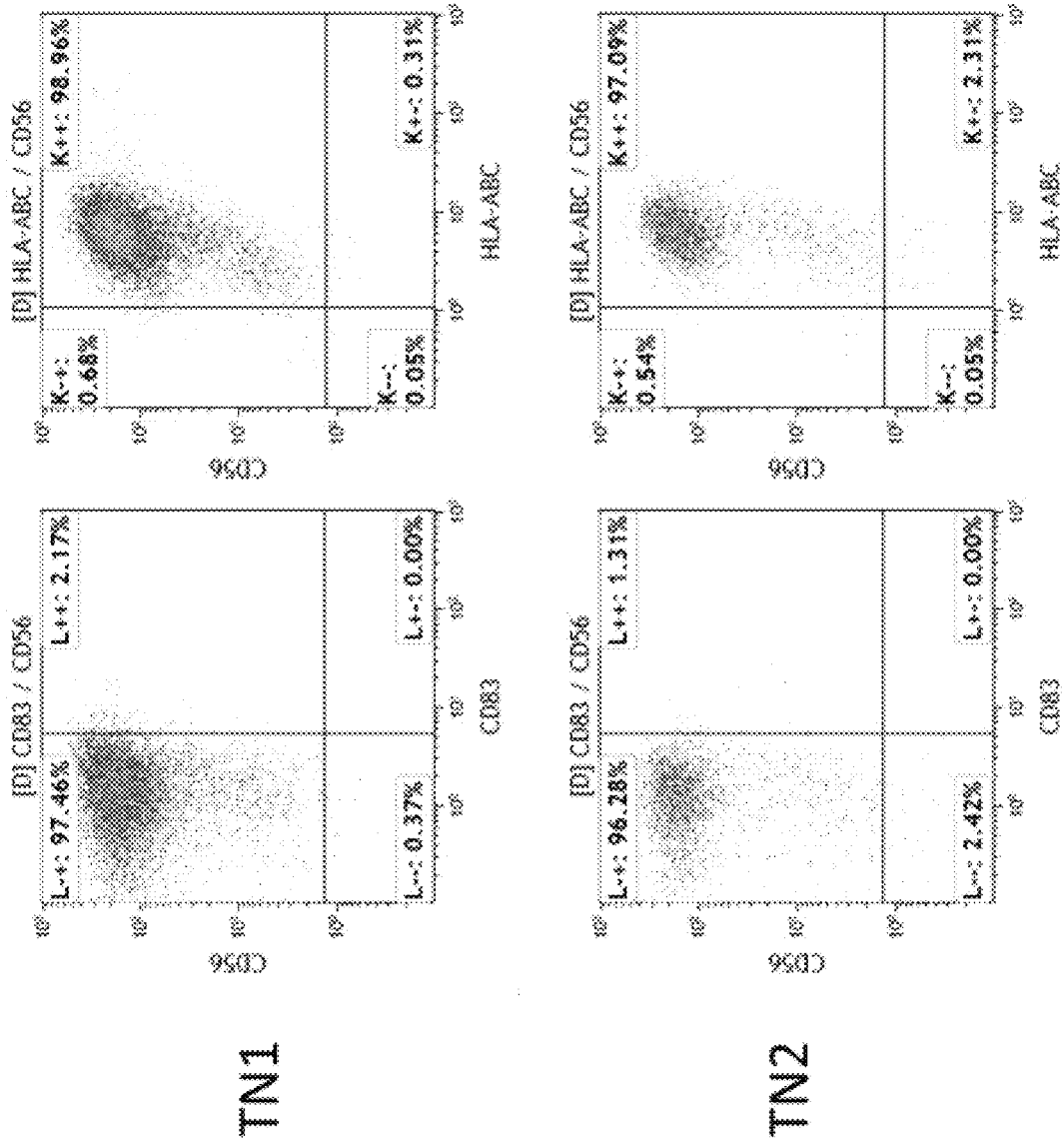

As shown in FIGS. 2B and 2C, phenotypic analysis showed the similar pattern of the cultured cells generated from TN1 and TN2 initial cells.

Therefore, although the cultured cells generated from TN1 initial cells expressed comparable NK and DC phenotypes as those from TN2 initial cells as $CD3^-CD14^-CD19^-CD56^{hi}CD16^{dim}NKG2D^+CD11c^+HLA-DR^+CD86^+CD83^-$, TN1 initial cells ($CD3^-CD14^-CD19^-$) gave highly pure cultured cells with better yields than from using TN2 initial cells ($CD25^-CD14^-CD19^-$).

Example 3: Dispensable Role of IFN-γ

WO2015/100495 disclosed that IFN-γ is crucial for the generation of the modified NK cells with both NK cell and DC cells function. However, we surprisingly found that IFN-γ had little effect in the generation of the modified NK cells disclosed herein.

$1 \times 10^6$/mL of $CD3^-CD14^-CD19^-$ mononuclear cells were cultured in the presence of 30 ng/mL hIL-15, 3 ng/mL hIL-12, and with or without 45 ng/mL hIFN-γ for 9 days. The cultured cells were stained with mAbs of CD45-ECD, CD3-APC-Alexa Flour 750, CD14-APC-Alexa Flour 750, and CD19-APC-Alexa Flour 750 (Beckman Coulter). Samples were acquired and analyzed via Navios Flow Cytometer while the data analysis was done via Kaluza software (Beckman Coulter).

Figure 3A:
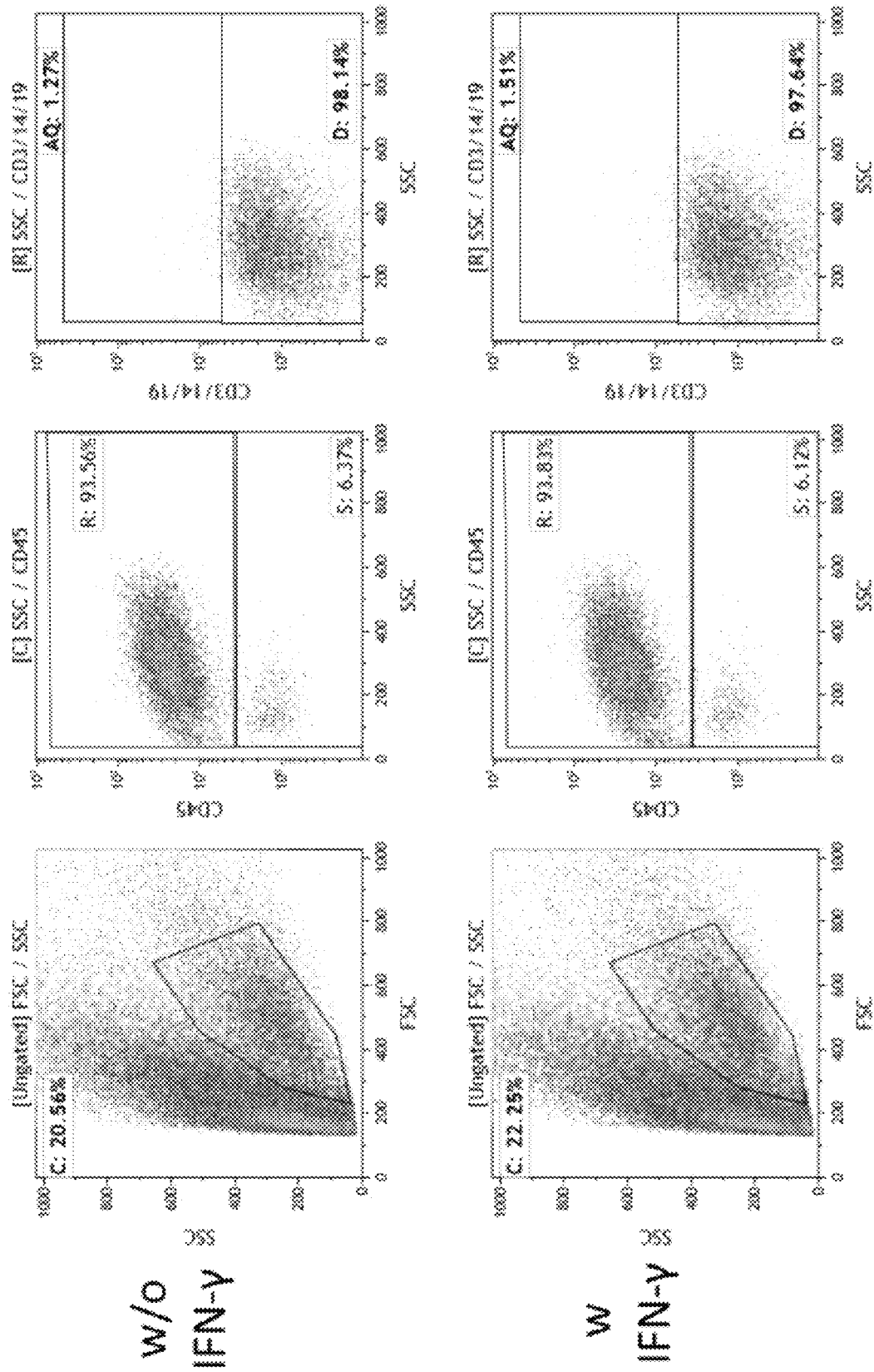
FIG. 3A illustrates an assembly of flow cytometry images of the modified NK cells cultured with or without IFN-γ for expression of CD45, CD3, CD14, and CD19.
Figure 3B:
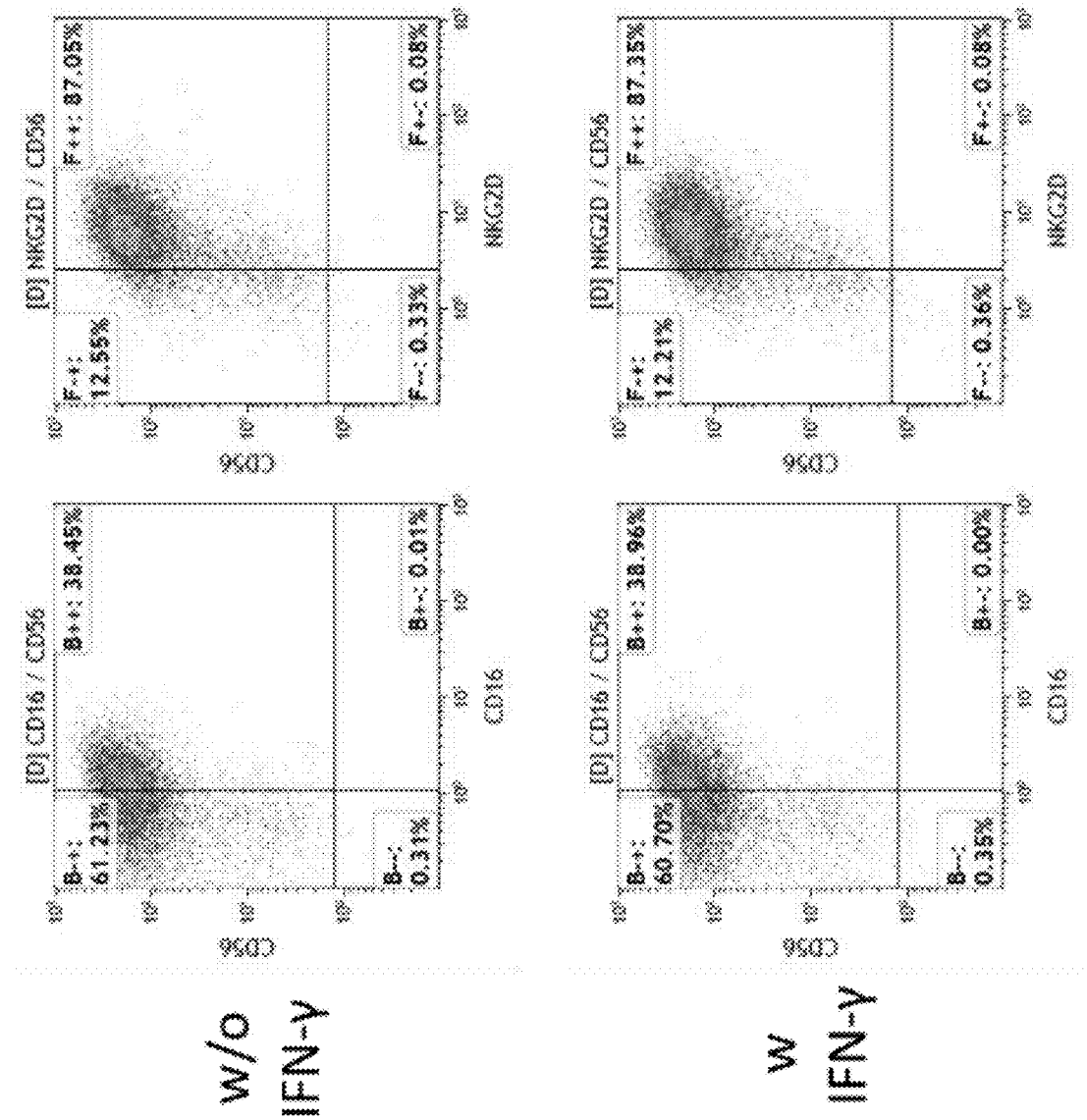
FIGS. 3B and 3C illustrate an assembly of flow cytometry images of the modified NK cells cultured with or without IFN-γ for NK phenotypes and DC phenotypes, respectively.
Figure 3C:
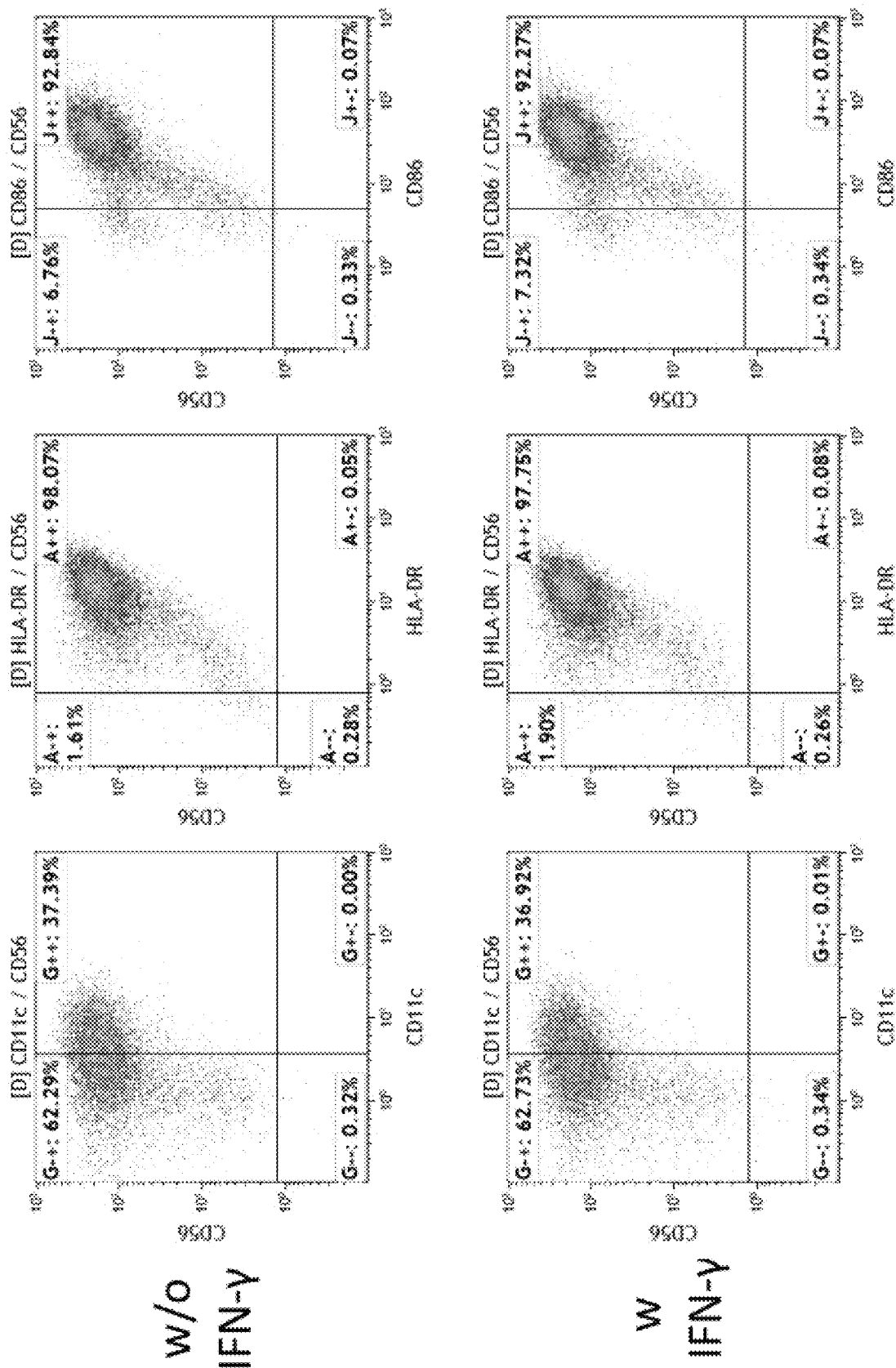
Figure 3C:
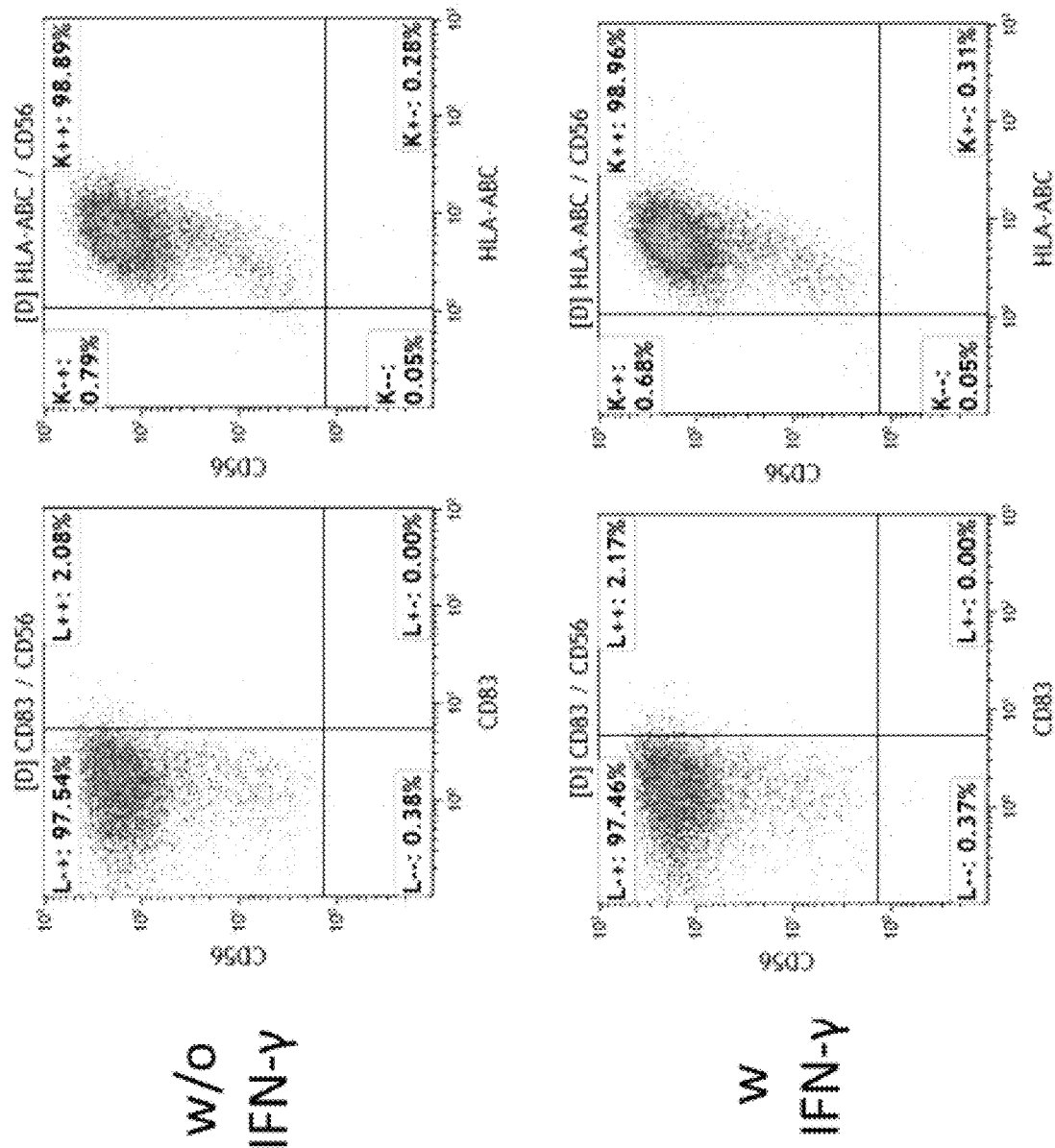

As shown in FIG. 3A and Table 4, the cells cultured with or without IFN-γ generated substantially the same purity and yields on the cultured cells, indicating that emergence of the cultured cells from TN1 initial cells was in an IFN-γ-independent manner. In addition, phenotypic analysis showed the similar pattern of the cultured cells with or without IFN-γ (FIGS. 3B and 3C).

TABLE 4

| Cells | Purity | Yields (cells) |
|---|---|---|
| w/o IFN-γ | 91.82% | $1.22 \times 10^7$ |
| w IFN-γ | 91.61% | $1.22 \times 10^7$ |

As a result, IFN-γ shed less effect onto emergence of the cultured cells disclosed herein in terms of cell purity, yields and acquisition of NK and DC phenotypes.

Example 4: Treatment Period of IL-12

$CD3^-CD14^-CD19^-$ mononuclear cells were cultured with 30 ng/mL hIL-15 for 12 days and in the presence of 3 ng/mL hIL-12 for 9 or 12 days. The cells were sub-cultured on day 6 and the medium was changed every three days. The cultured cells were counted by using trypan blue dye exclusion. In addition, the cultured cells were stained with mAbs of NKG2D-PE, CD45-ECD, CD16-PE-Cy7, CD56-APC-Alexa Flour 700, CD3-APC-Alexa Flour 750, CD14-APC-Alexa Flour 750, CD19-APC-Alexa Flour 750 (Beckman Coulter), CD86-Alexa488, CD83-PE-Cy5, CD11c-APC, and HLA-ABC-Pacific Blue (Biolegend). Samples were acquired and analyzed via Navios Flow Cytometer while the data analysis was done via Kaluza software (Beckman Coulter).

Figure 4A:
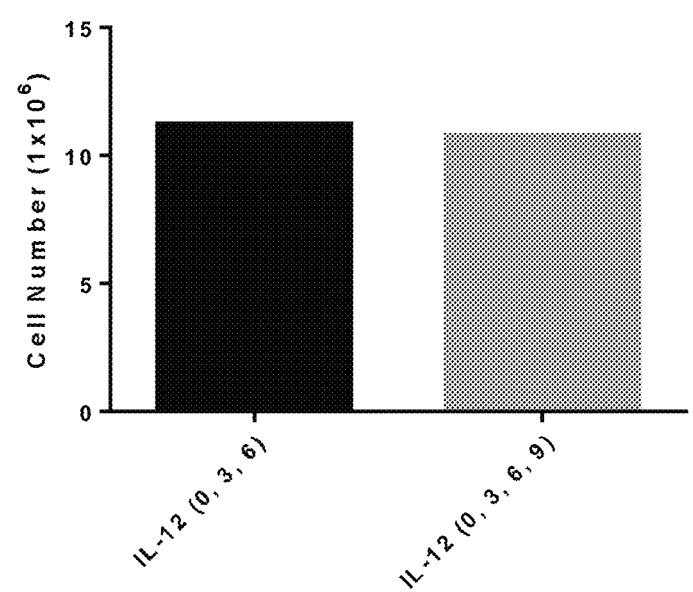
FIG. 4A illustrates cell numbers of the modified NK cells cultured with various IL-12 exposure periods.
Figure 4B:
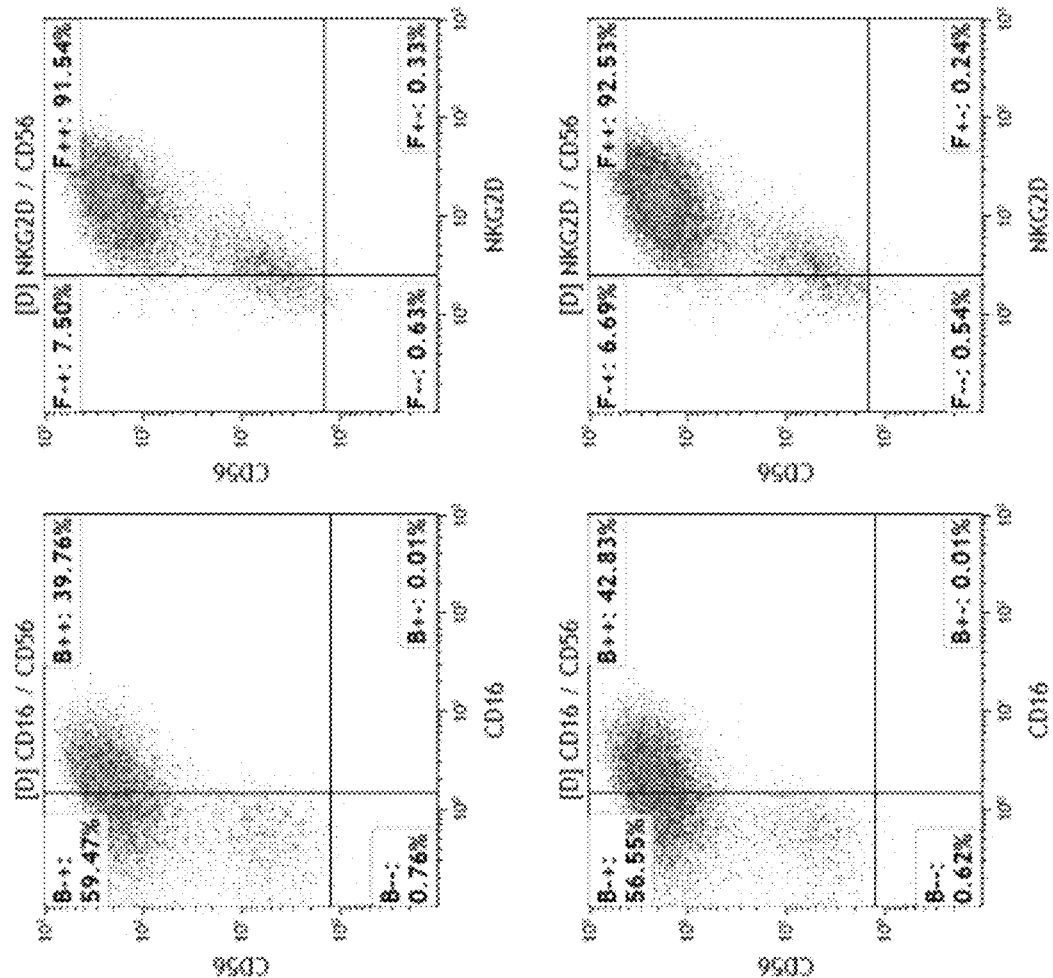
FIGS. 4B and 4C illustrate an assembly of flow cytometry images of the modified NK cells cultured with various IL-12 exposure periods for NK phenotypes and DC phenotypes, respectively.
Figure 4C:
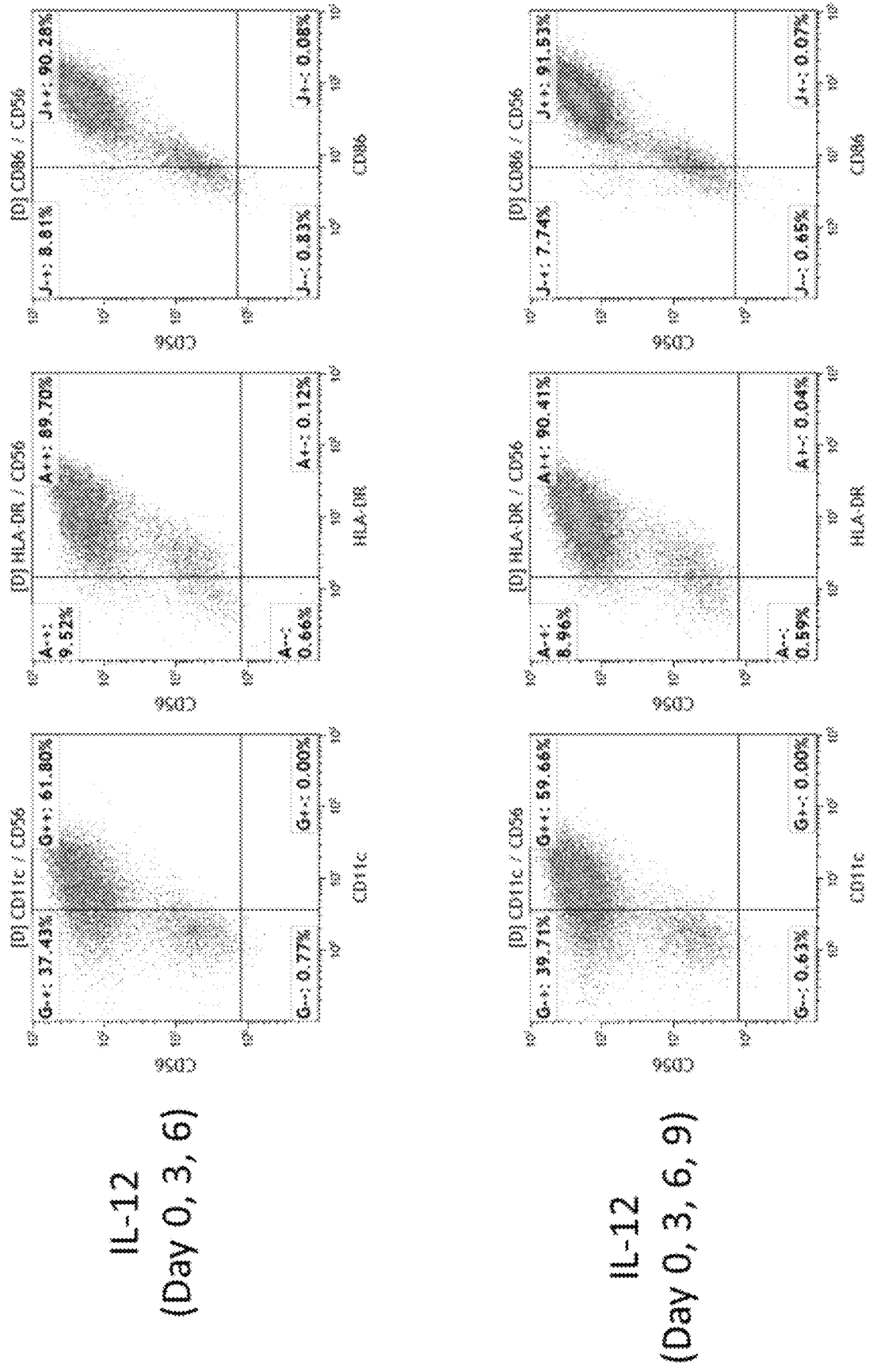

As shown in FIG. 4A, prolong exposure of IL-12 for 12 days shed less effect onto emergence of the cultured cells in terms of cell yields as compared to the cells with IL-12 exposure for 9 days. Similarly, phenotypic analysis showed the similar pattern of the cultured cells with IL-12 exposure for 9 days or 12 days (FIGS. 4B and 4C).

On the other hand, functional assays were also performed to evaluate cytotoxicity and antigen-presentation activity. Evaluation of cytotoxicity of the modified NK cells was performed by PanToxilux kit (OncoImmunin, Inc.). Human chronic myelogenous leukemia (CML) cell line, K562, served as a target cell and stained with TFL4 under the optimal concentration for 50 minutes. Co-incubation of TFL4 labeled target cell and the cultured cells with the caspase substrate under 37° C. for 20 minutes. The cells were harvested and analyzed the signal of TFL-4$^+$ substrate$^+$ via flow cytometry. Evaluation of the activity of antigen-presentation of the cultured cells was performed by mixed lymphocyte reaction (MLR). Responder cells (CD25$^-$ PBMCs) were enriched and stained with CellTrace™ CFSE cell proliferation kit (Invitrogen). Co-culture of CSFE-labeled CD25$^-$ PBMCs and the modified NK cells under 37° C. for 5 days. hIL-2 and hIL-15 were added on day 1 and day 3 to reduce the threshold of TCR engagement. The cells were harvested and analyzed the CFSE-diluted pattern via flow cytometry.

Figure 4D:
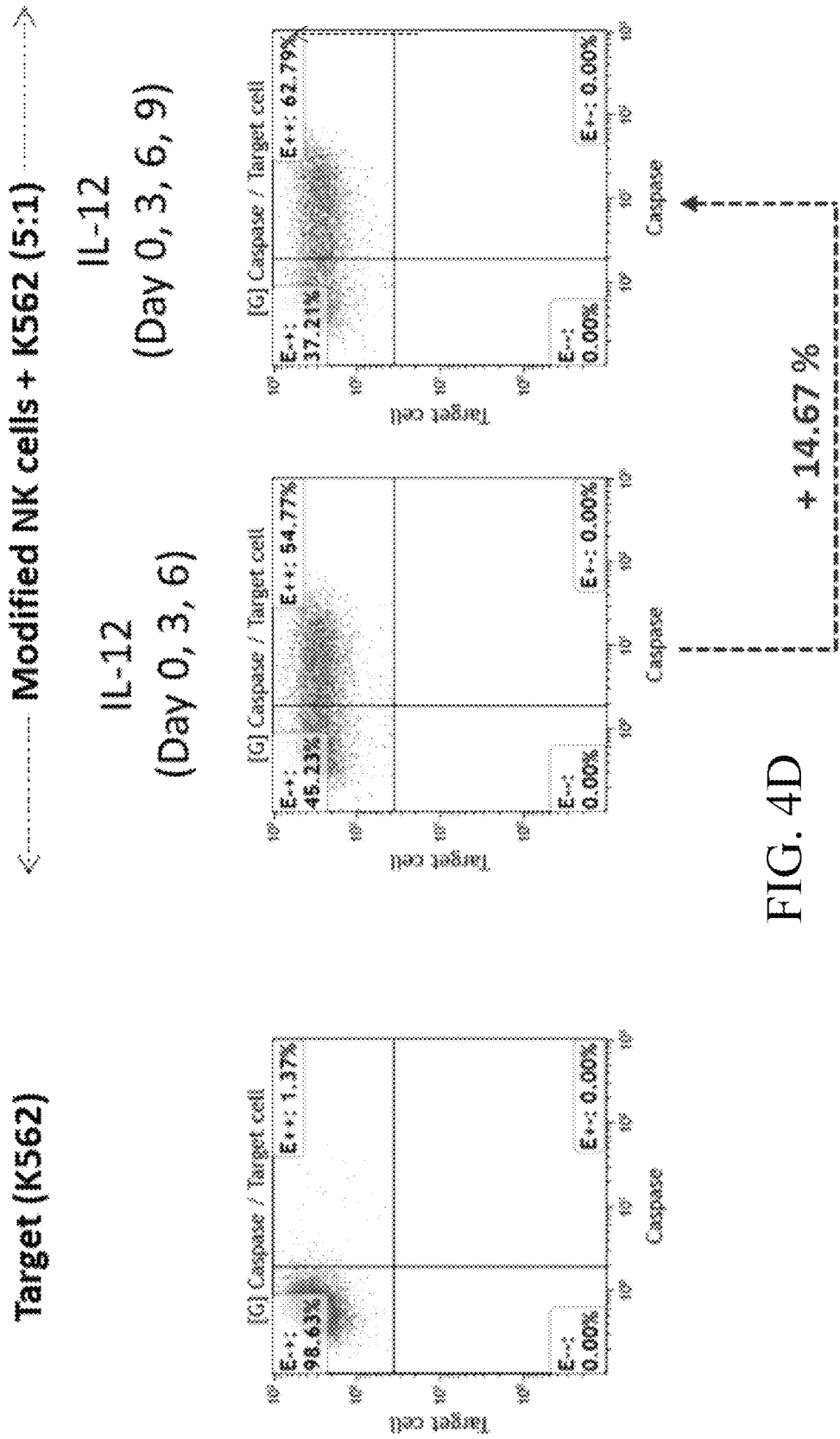
FIG. 4D is an assembly of flow cytometry images illustrating the cytotoxicity of the modified NK cells.
Figure 4E:
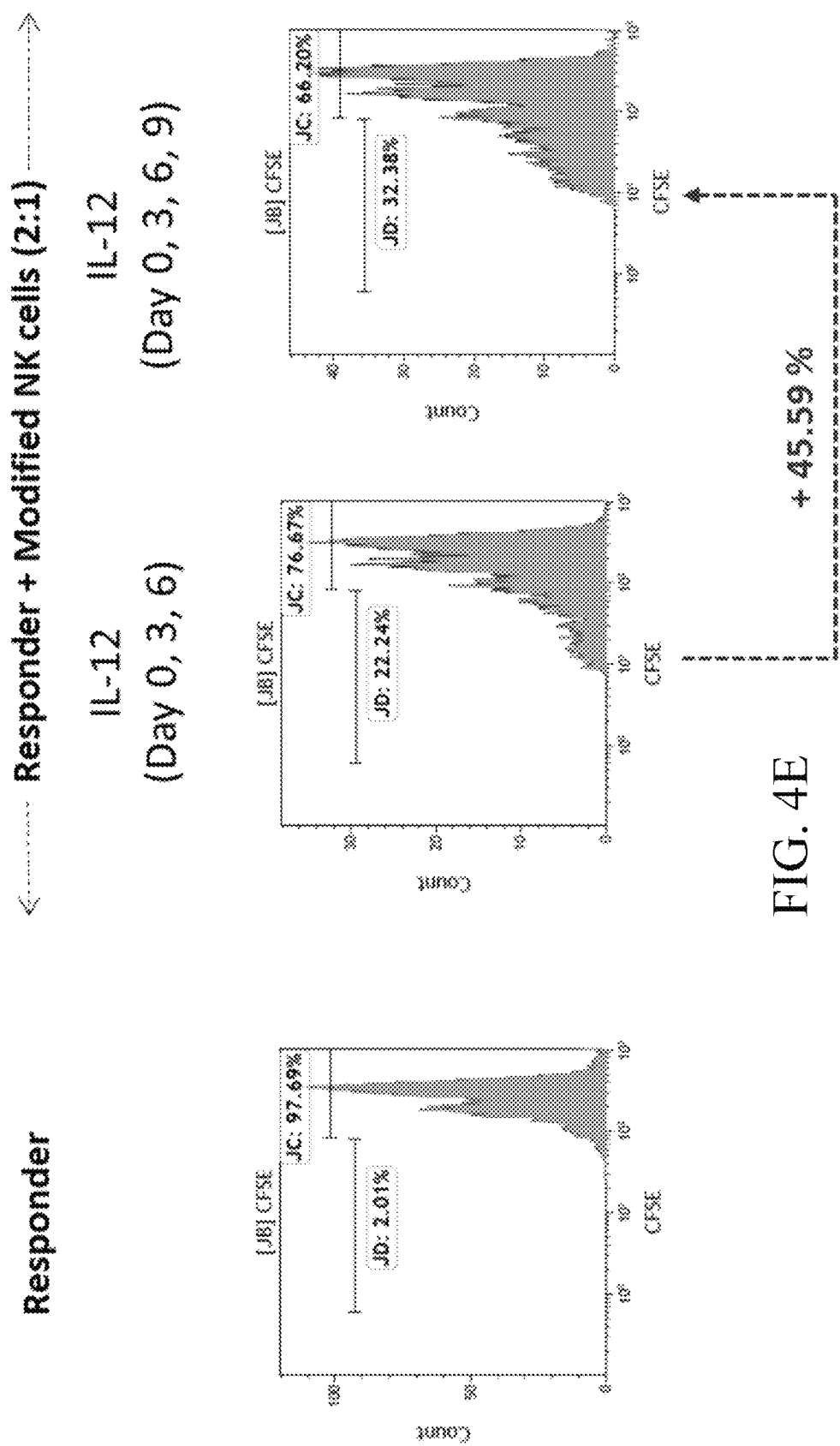
FIG. 4E is an assembly of flow cytometry analysis of cell division illustrating the antigen presenting call (APC) activities of modified NK cells on T lymphocyte proliferation.

As shown in FIGS. 4D and 4E, prolong exposure of IL-12 for 12 days augmented cytotoxicity and antigen-presenting cell activities of the cultured cells as compared to the cells with IL-12 exposure for 9 days.

As a result, although prolonged IL-12 exposure shed less effect onto emergence of the cultured cells disclosed herein in terms of cell purity, yields and acquisition of NK and DC phenotypes, cytotoxicity and antigen-presenting cell activities of the modified NK cells were indeed augmented with prolong IL-12 exposure for 12 days.

Example 5: Effects of IL-18 onto Emergence of the Modified NK Cells

CD3$^-$CD14$^-$CD19$^-$ mononuclear were cultured in the presence of 30 ng/mL hIL-15, 3 ng/mL hIL-12, and 0, 50, 100 or 200 ng/mL of hIL-18 for 12 days. The cells were sub-cultured on day 6 and the medium was changed every three days. The cultured cells were harvested on day 3, 6, 9 and 12 and counted by using trypan blue dye exclusion. In addition, the cultured cells on day 3 and day 12 were harvested and stained with mAbs of against NKG2D-PE, CD45-ECD, CD16-PE-Cy7, CD56-APC-Alexa Flour 700, CD3-APC-Alexa Flour 750, CD14-APC-Alexa Flour 750, CD19-APC-Alexa Flour 750 (Beckman Coulter), CD86-Alexa488, CD83-PE-Cy5, CD25-PerCP/Cyanine5.5 CD11c-APC, and HLA-ABC-Pacific Blue (Biolegend). Samples were acquired and analyzed via Navios Flow Cytometer while the data analysis was done via Kaluza software (Beckman Coulter).

Figure 5A:
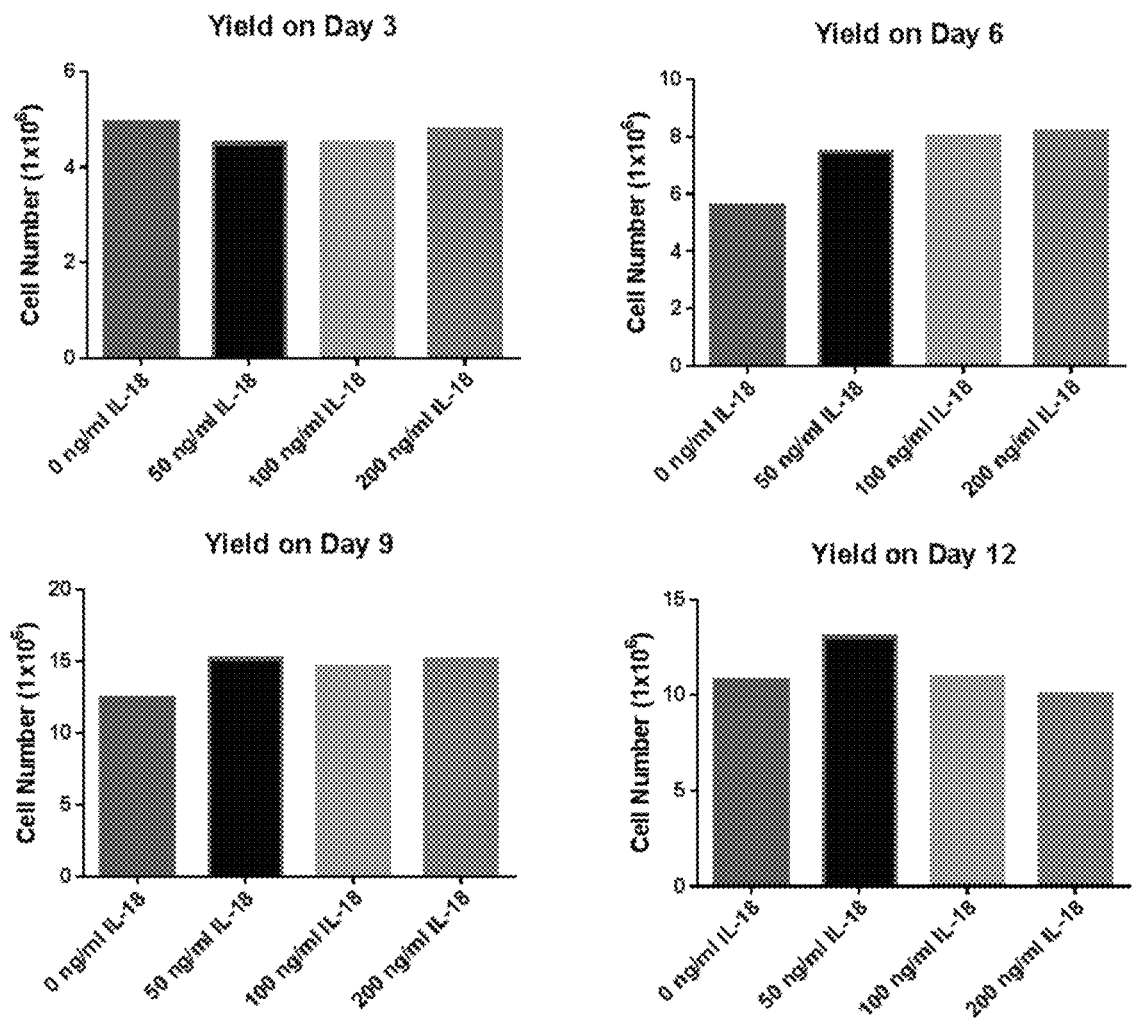
FIG. 5A illustrates cell numbers of the modified NK cells cultured with various IL-18 exposure concentrations.
Figure 5B:
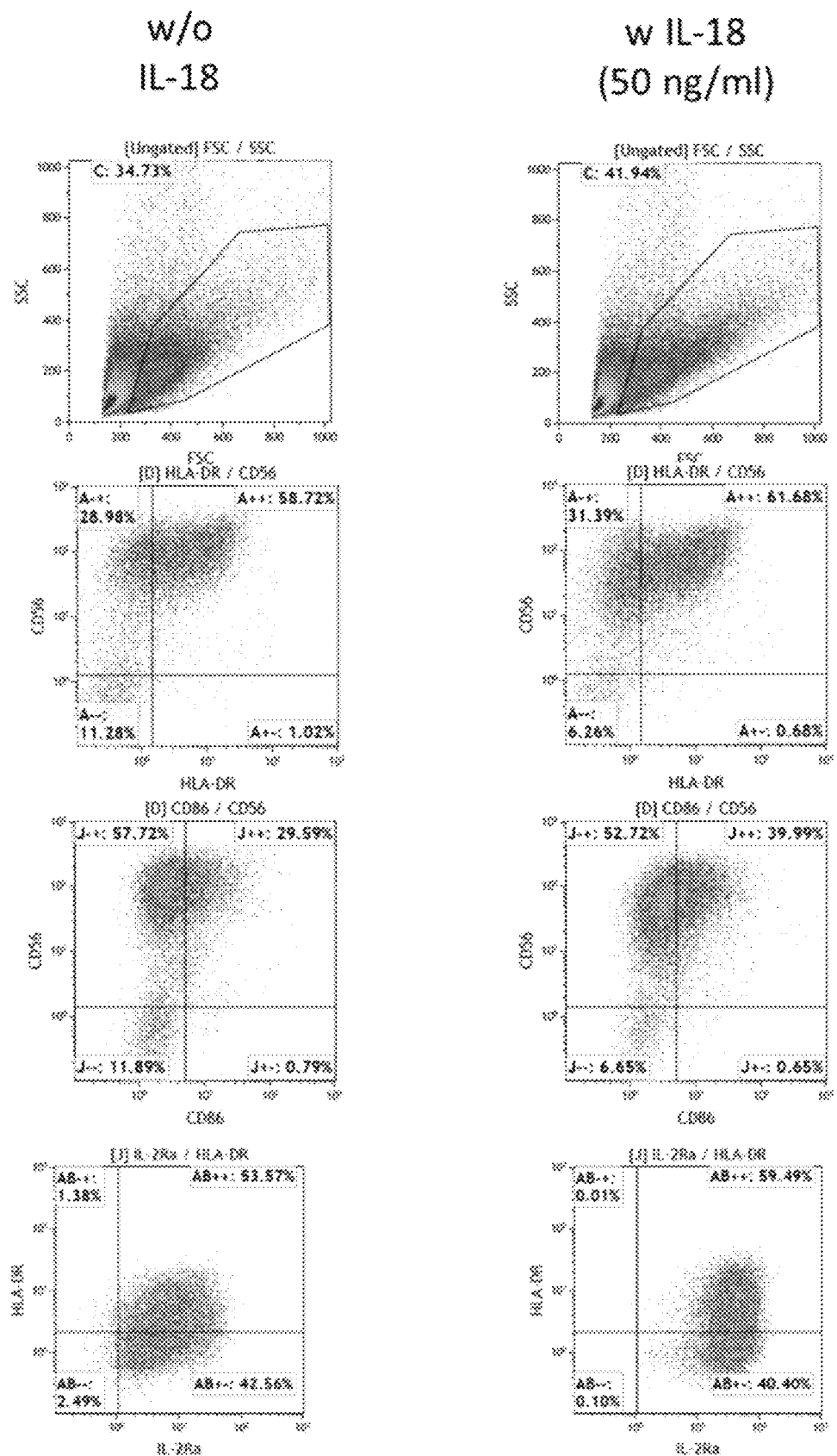
FIG. 5B illustrates an assembly of flow cytometry images of up-regulation of expression of CD25, HLA-DR and CD86 of the modified NK cells on day 3.
Figure 5B:
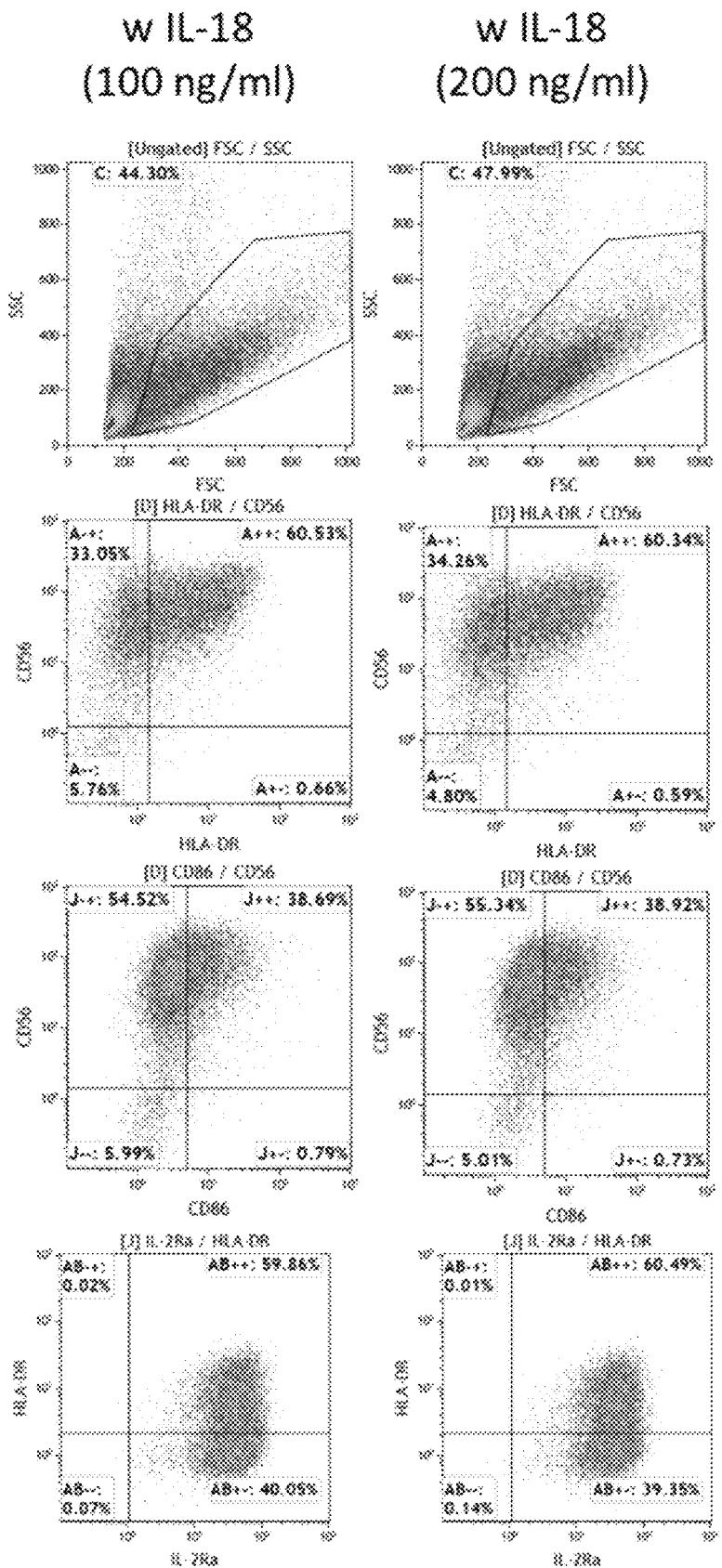
Figure 5C:
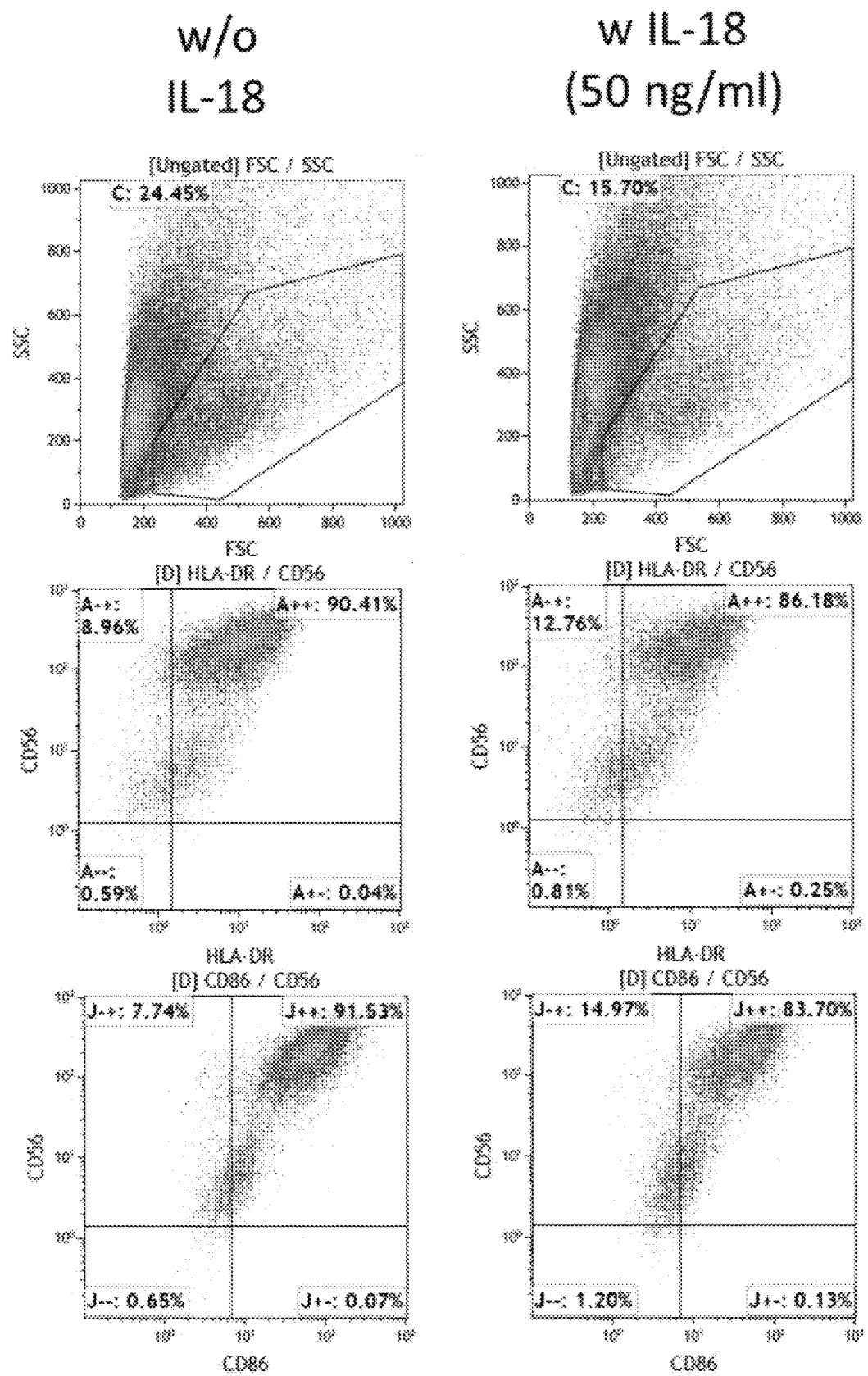
FIG. 5C illustrates an assembly of flow cytometry images of down-regulation of HLA-DR and CD86 of the modified NK cells on day 12.
Figure 5C:
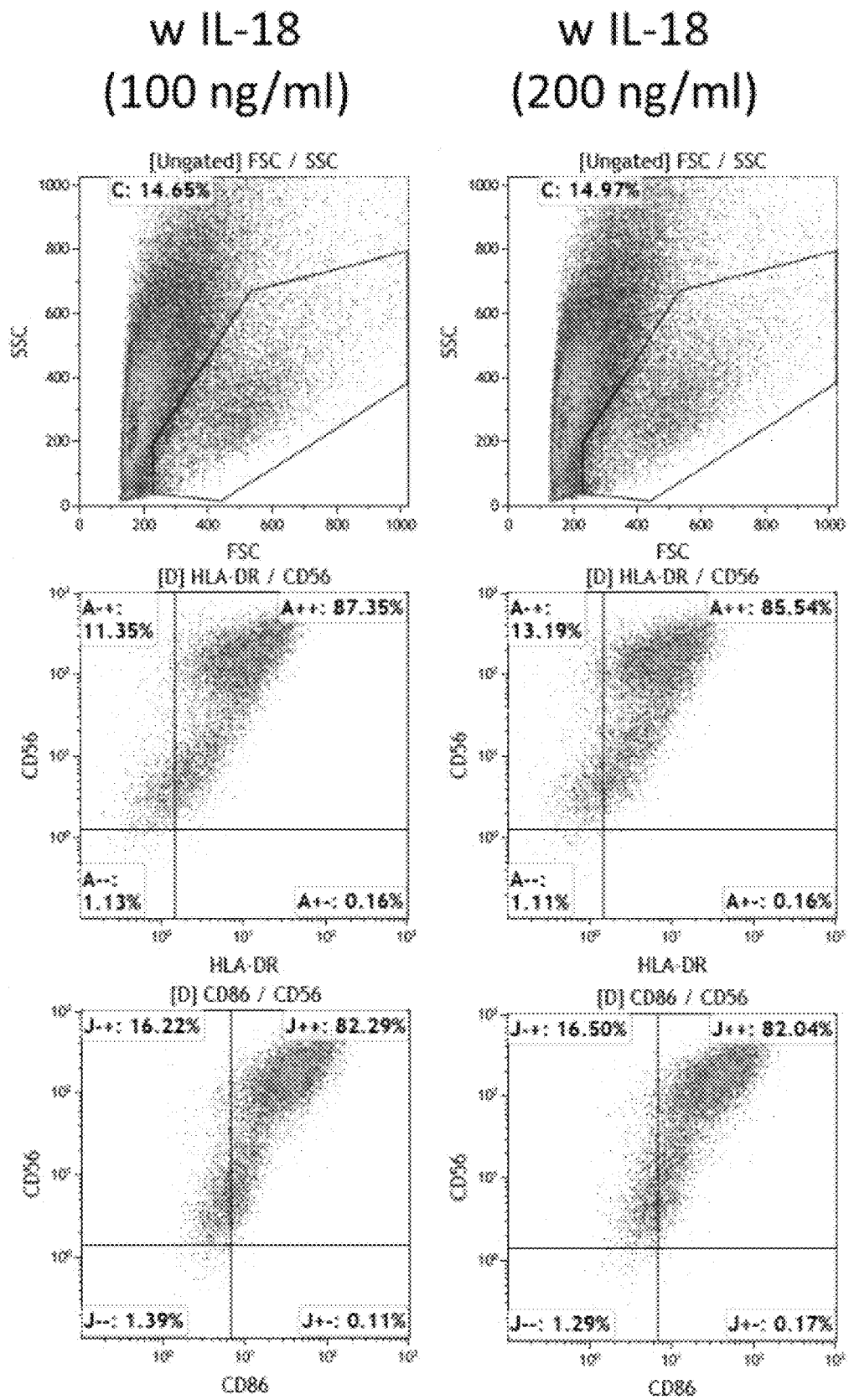

As shown in FIG. 5A, addition of IL-18 augmented expansion of the cultured cells after day 6 and until day 12. Unexpectedly, phenotypic analysis showed that addition of IL-18 up-regulated the expression of CD25, HLA-DR and CD86 of the on day 3 (FIG. 5B). However, the expression of HLA-DR and CD86 was down-regulated on day 12 (FIG. 5C).

Figure 5D:
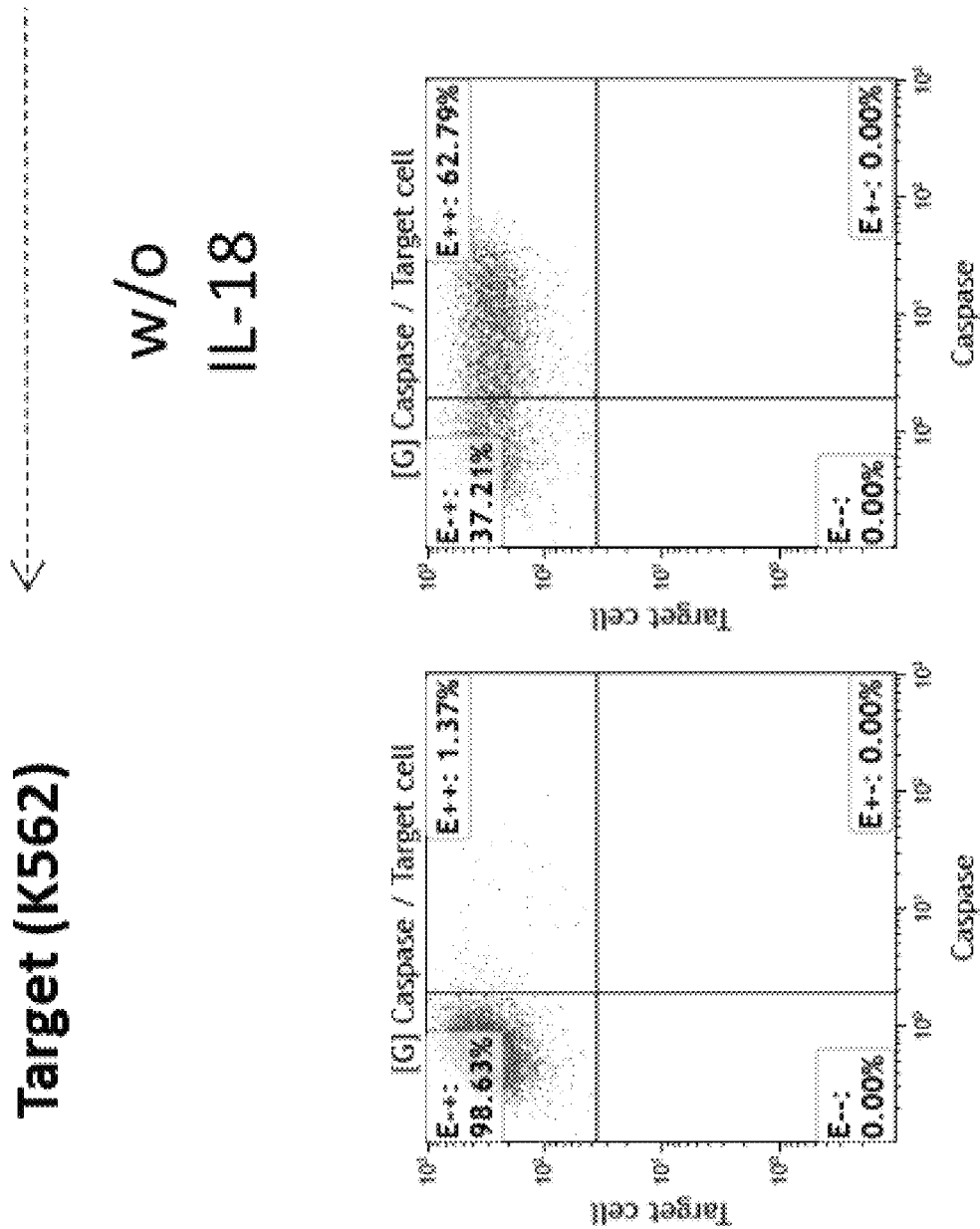
FIG. 5D is an assembly of flow cytometry images illustrating the cytotoxicity of the modified NK cells cultured with IL-18.
Figure 5D:
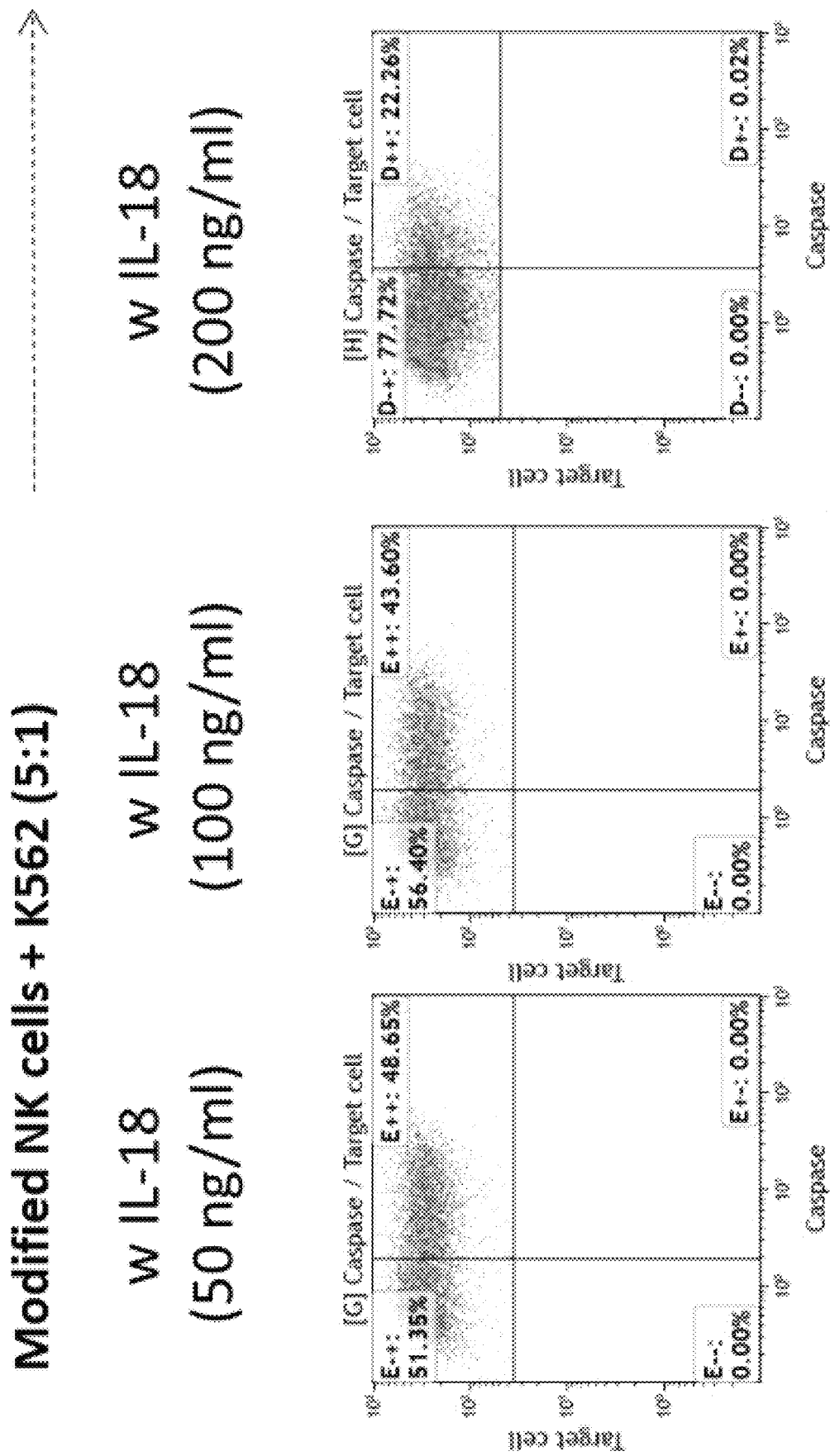
Figure 5E:
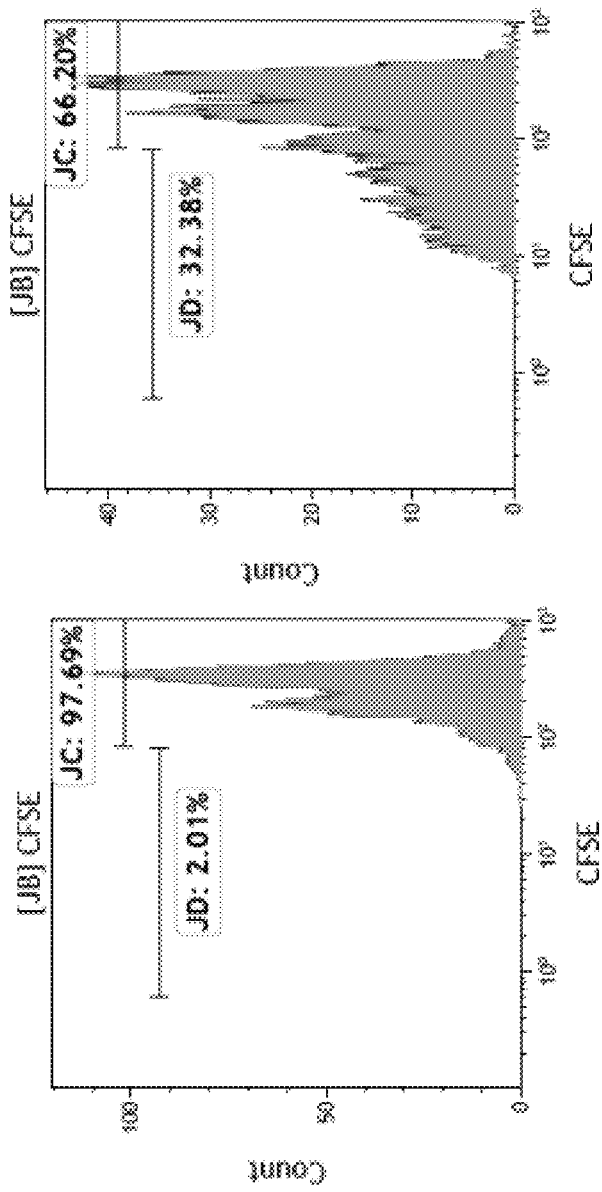
FIG. 5E is an assembly of flow cytometry analysis of cell division illustrating the APC activities of the modified NK cells cultured with IL-18 on T lymphocyte proliferation.
Figure 5E:
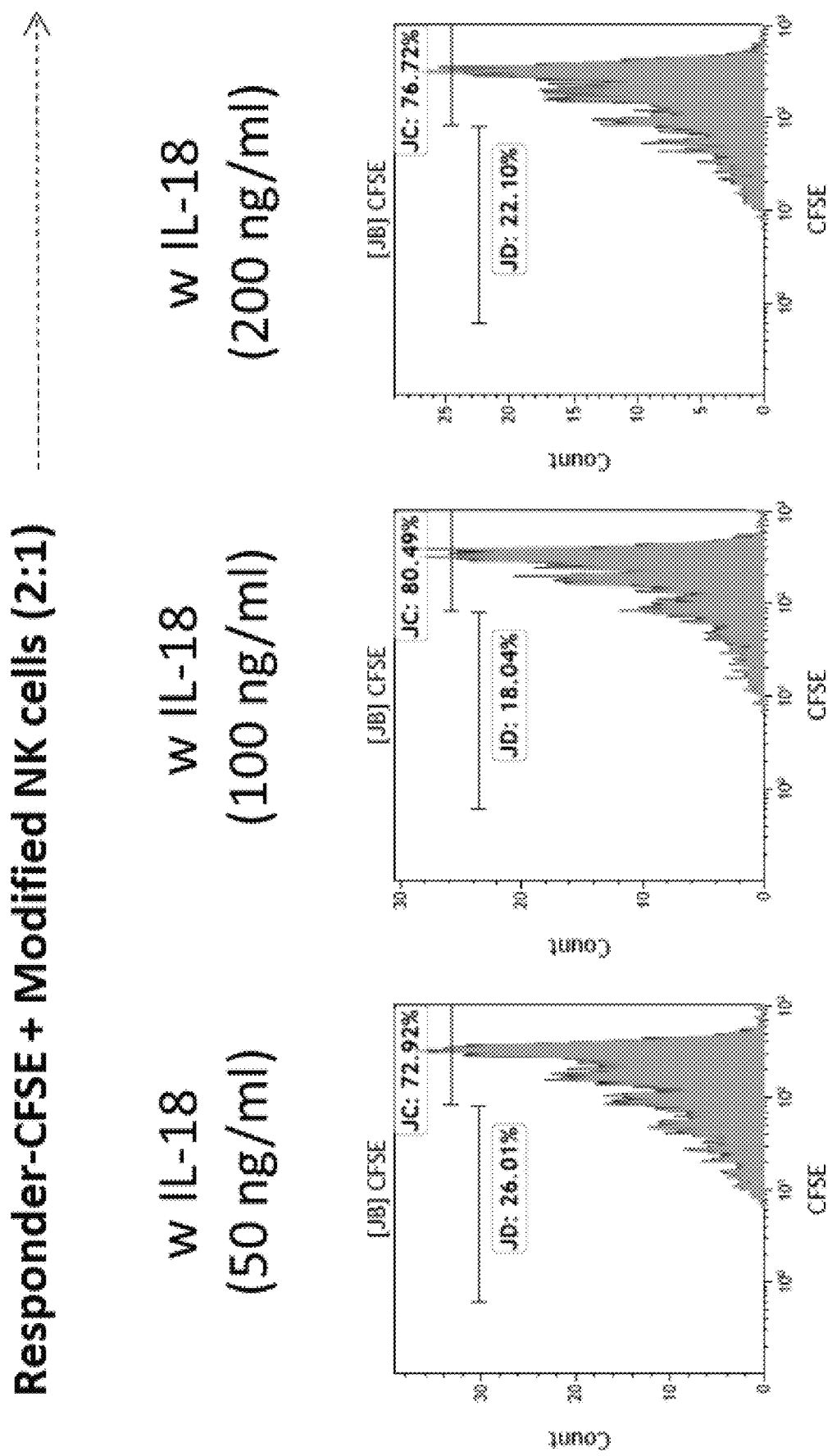

Similarly, functional assays were also performed to evaluate cytotoxicity and antigen-presentation activity of the cultured cell treated with varied doses of IL-18. According to FIGS. 5D and 5E, addition of IL-18 negatively regulated cytotoxicity and antigen-presenting cell activities of the cultured cells on day 12.

As a result, addition of 50 ng/mL IL-18 augmented expression of CD25, HLA-DR and CD86 of the modified NK cells on day 3 with cell population expansion of the modified NK cells until day 12. However, long term IL-18 exposure may have the opposite effects on cell size, phenotype and function of the modified NK cells. Therefore, the adequate exposure periods of IL-18 might be critical for the modified NK cells generation.

Example 6: Treatment Period of IL-18

CD3$^-$CD14$^-$CD19$^-$ mononuclear were cultured in the presence of 30 ng/mL hIL-15, 3 ng/mL hIL-12 for 12 days. Kinetic exposure of 50 ng/mL hIL-18 on day 0, 3 and 6. The cells were sub-cultured on day 6 and the medium was changed every three days. The cultured cells were harvested on day 3, 6, 9, 12 and 15 and counted by using trypan blue dye exclusion.

Similarly, functional assays were also performed to evaluate cytotoxicity and antigen-presentation activity of the cultured cell treated with varied periods of IL-18.

Figure 6A:
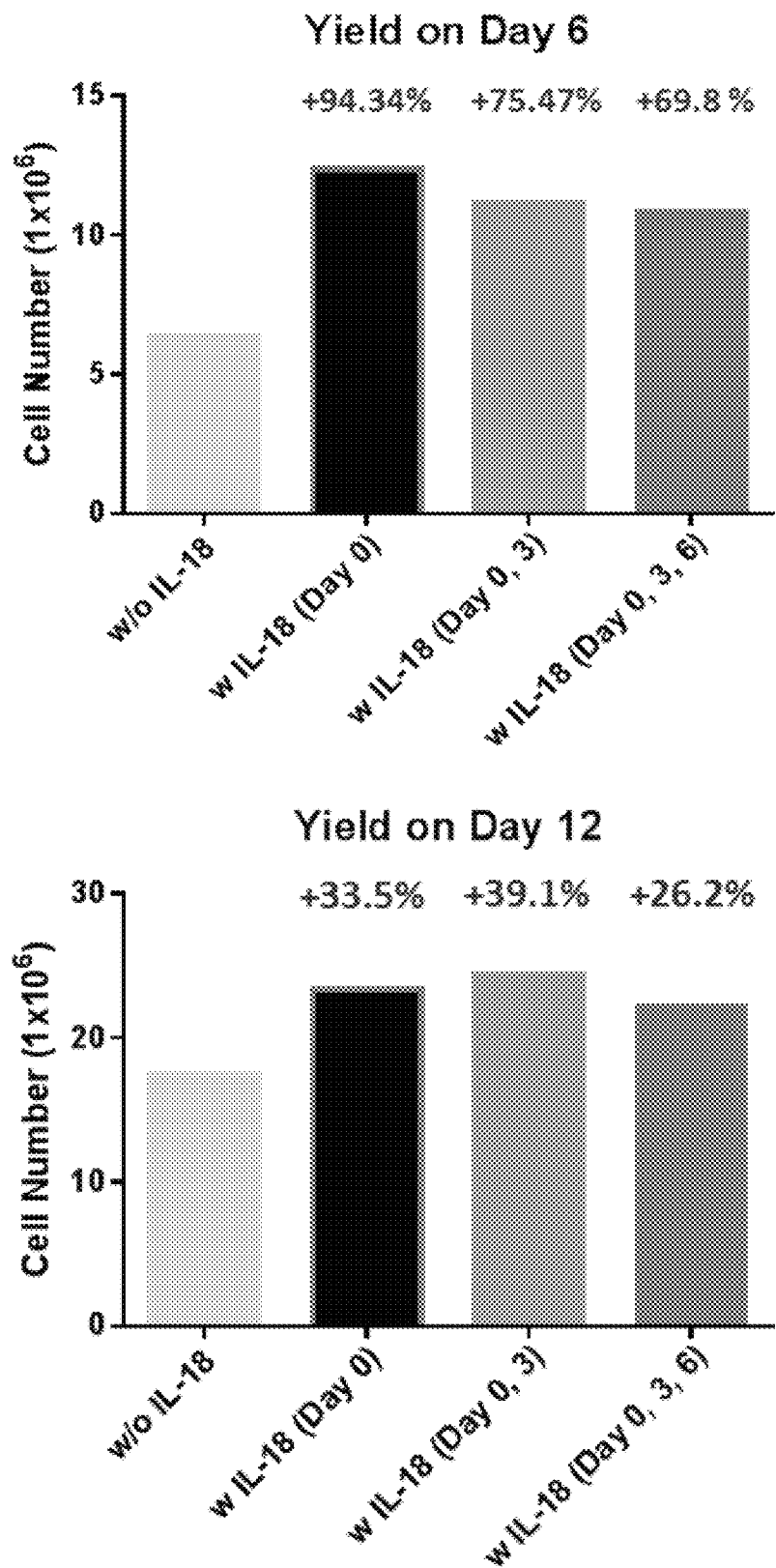
FIG. 6A illustrates cell numbers of the modified NK cells cultured with various IL-18 exposure periods.
Figure 6A:
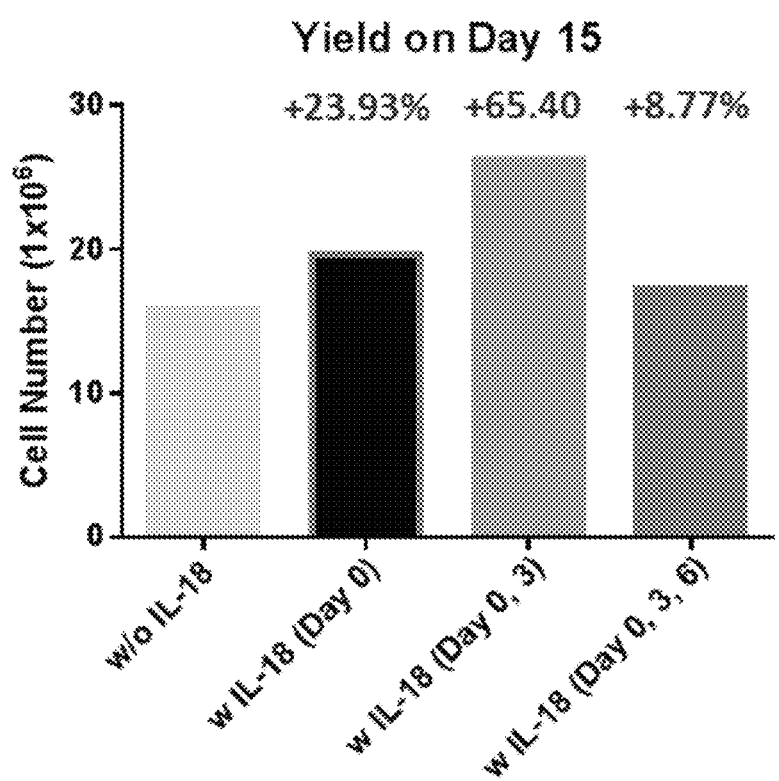
Figure 6B:
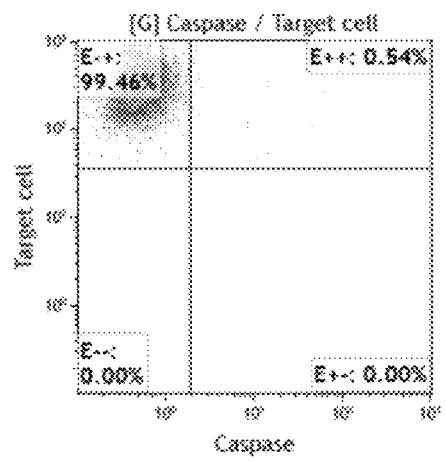
FIG. 6B is an assembly of flow cytometry images illustrating the cytotoxicity of the modified NK cells cultured with various IL-18 exposure periods.
Figure 6B:
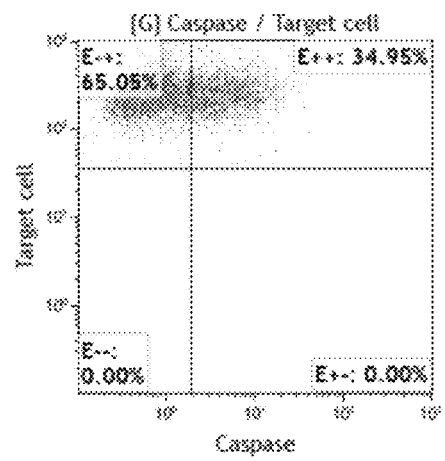
Figure 6B:
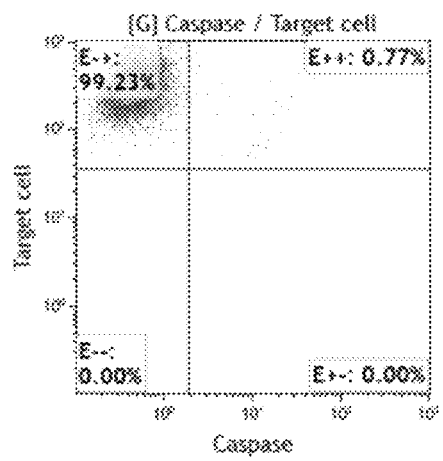
Figure 6B:
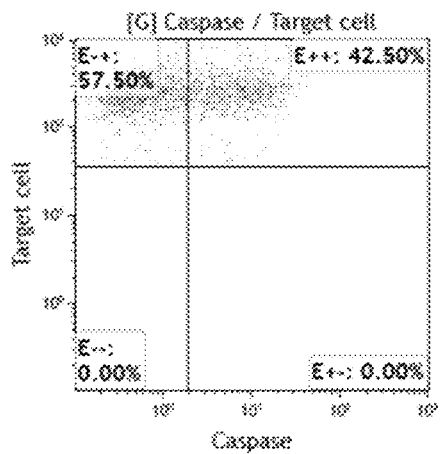
Figure 6B:
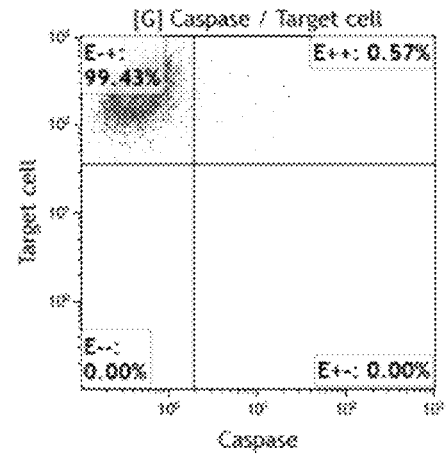
Figure 6B:
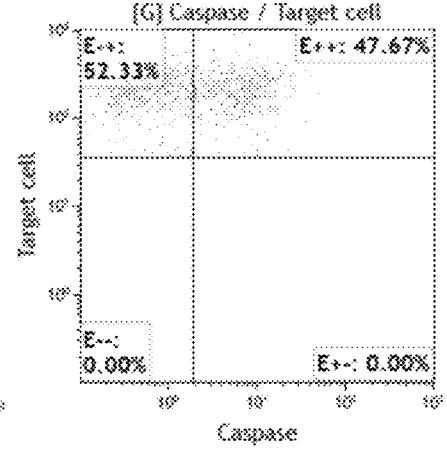
Figure 6B:
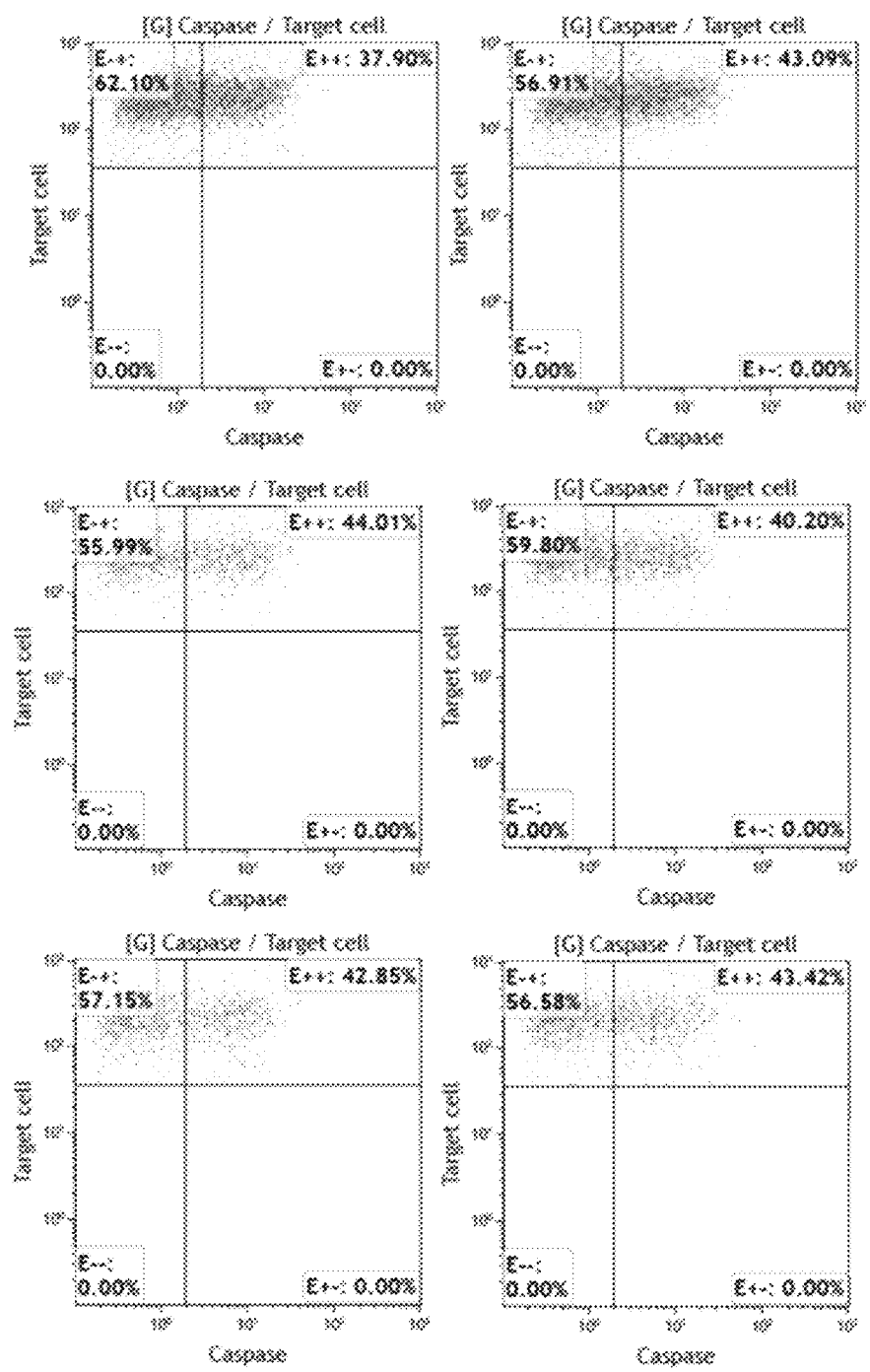
Figure 6B:
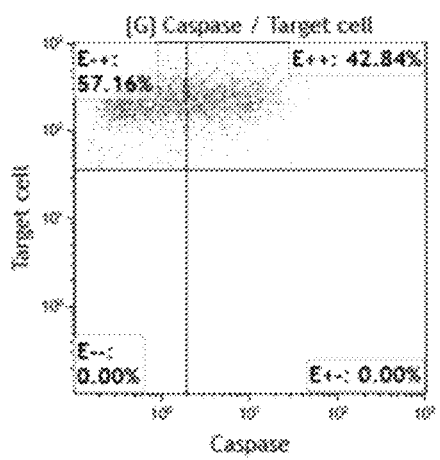
Figure 6B:
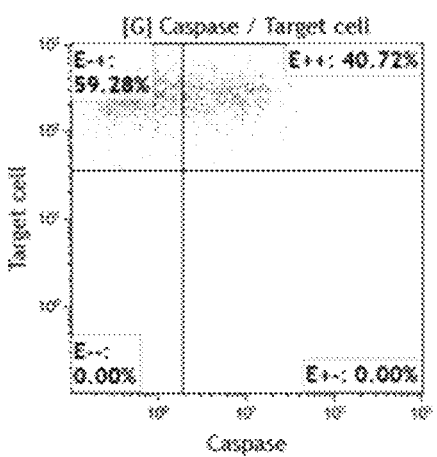
Figure 6B:
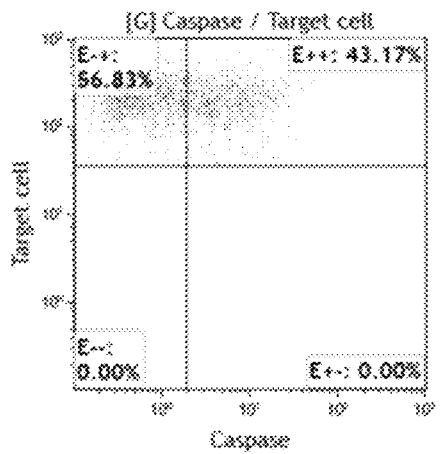
Figure 6C:
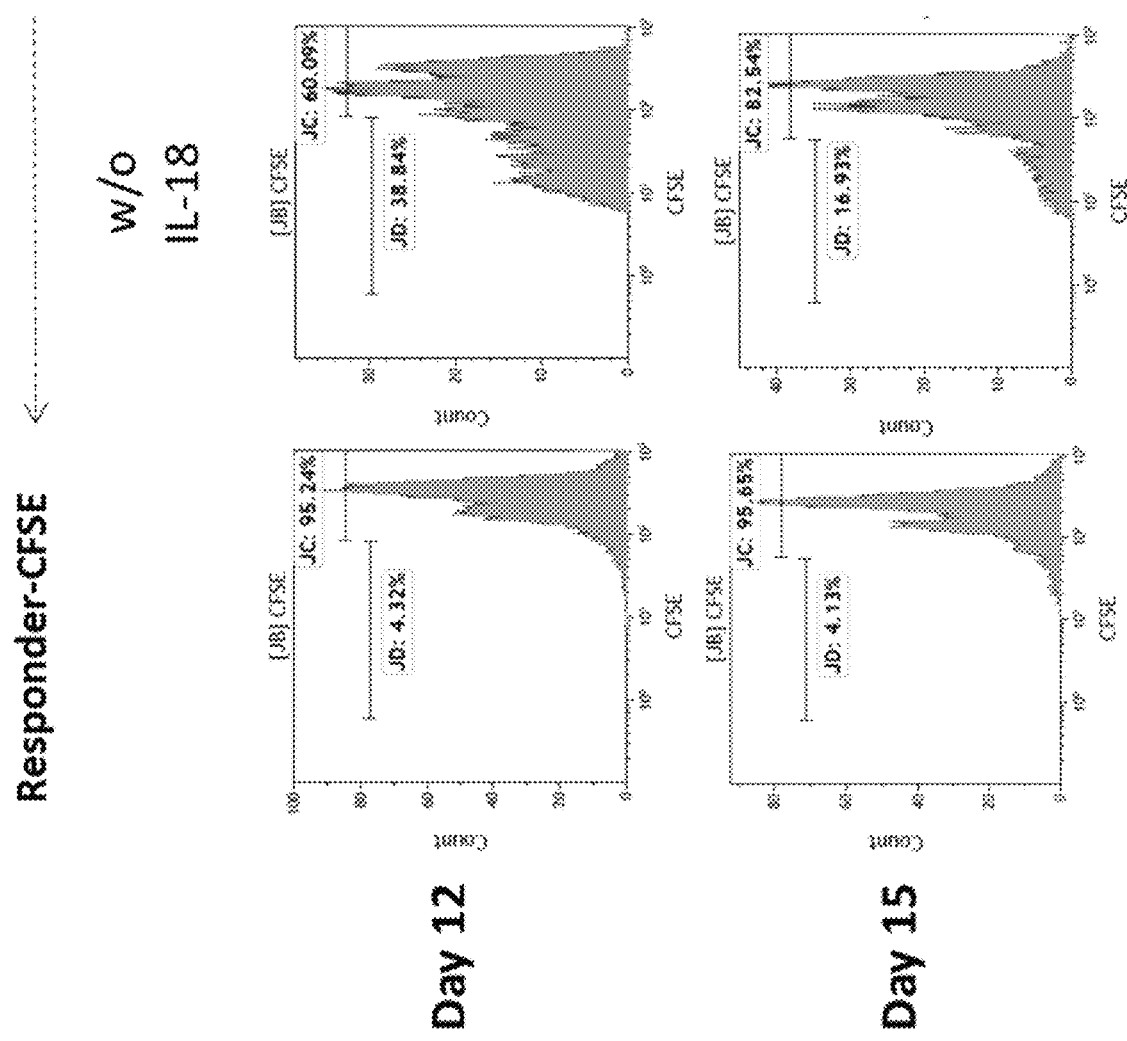
FIG. 6C is an assembly of flow cytometry analysis of cell division illustrating the APC activities of the modified NK cells cultured with various IL-18 exposure periods on T lymphocyte proliferation.
Figure 6C:
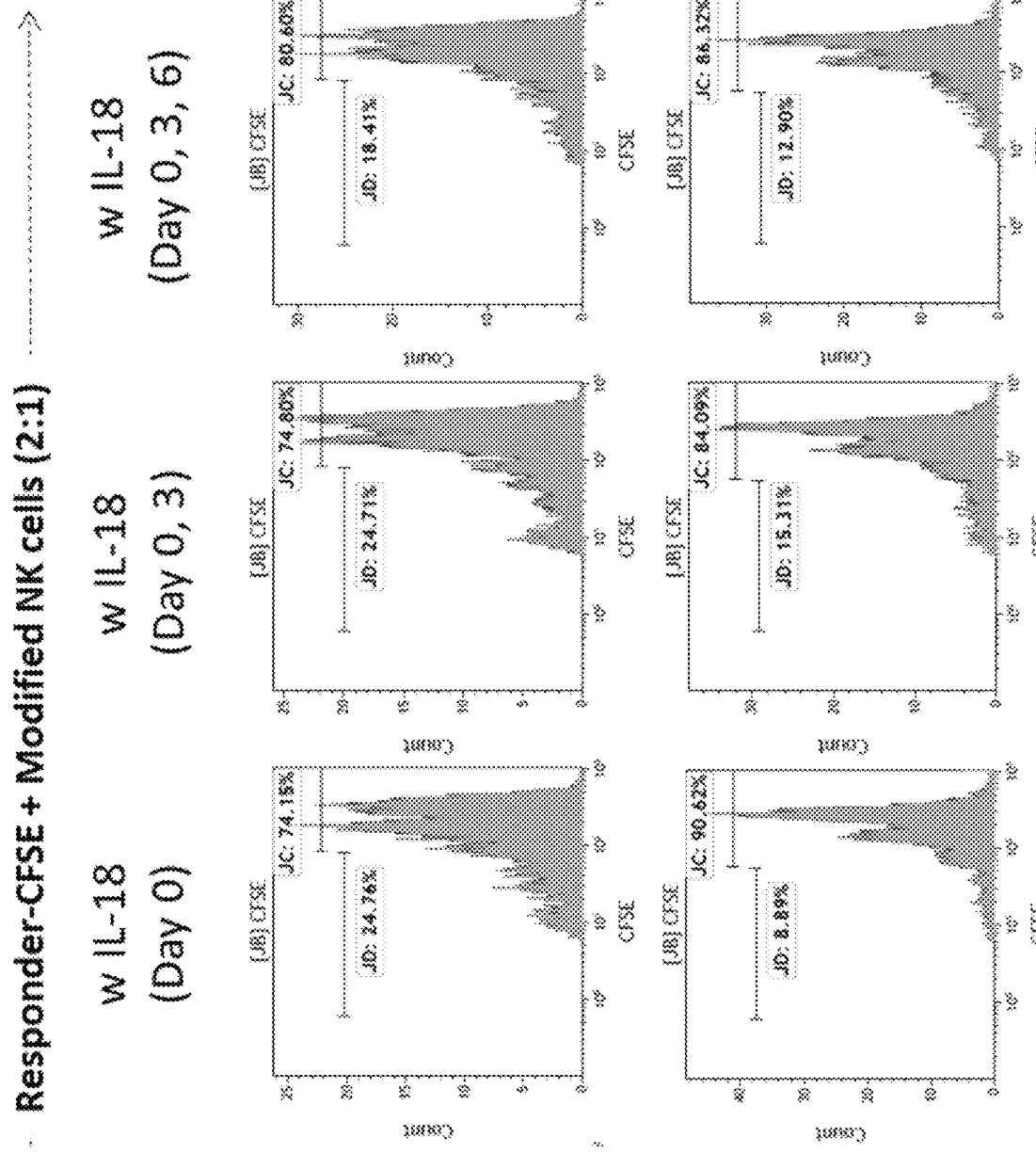

As shown in FIG. 6A, addition of IL-18 on day 0 and day 3 (i.e. exposure for 6 days) promoted best expansion of the cultured cells on day 15 than cells with addition of IL-18 on day 0 (i.e. exposure for 3 days) or day 0, 3 and 6 (i.e. exposure for 9 days). For cytotoxicity, exposure to IL-18 for 6 days promoted best cytotoxicity of the cultured cells on day 9 than exposure to IL-18 for 3 days or for 9 days (FIG. 6B). For antigen-presentation activity, exposure to IL-18 for 6 days promoted best antigen-presenting cell activities of the cultured cells on day 12 than exposure to IL-18 for 3 days or for 9 days (FIG. 6C).

On top of that, the antigen-presentation activity of the cultured cells exposed to IL-18 for 6 days reached maximum levels on day 12 and then significantly declined on day 15. As a result, the optimal culture period of the cultured cells under current cytokine niche was less than 15 days.

Example 7: Preparation of Initial Cell 40 mL of peripheral blood was collected from a healthy volunteer into vacuum tubes containing K2EDTA. The blood sample was mixed with equal volume of pre-warmed phosphate-buffered saline (PBS) (Biological Industries, Israel). The 40 mL diluted peripheral blood aliquot was placed into a 50 mL centrifuge tube and loaded 10 mL pre-warmed Ficoll-Paque™ PREMIUM. The centrifuge tube was centrifuged at 2000 rpm, in room temperature for 30 min. The mononuclear cells in the interface layer were collected and washed once in PBS. The cell pellet was re-suspended into a density of $10^6$ cells/100 mL MACS buffer.

To deplete CD14$^+$ cells, CD19$^+$ cells and CD3$^+$ cells, the mononuclear cells were subjected to immunomagnetic bead separation using "QuadroMACS Separator" (Miltenyi Biotec Bergisch, Gladbach, Germany), according to the manufacturer's instructions. Briefly, the mononuclear cells were reacted with biotin-anti-CD14, biotin-anti-CD19, and biotin-anti-CD3, separated with a magnetic separator, and the CD14$^-$, CD19$^-$ and CD3$^-$ cell fraction was purified from unbound cells by washing. The enriched mononuclear cell fraction was substantially free of CD14$^+$ cells, CD19$^+$ cells and CD3$^+$ cells.

Example 8: Modified NK Cell Culture

After negative depletion, the purified CD14⁻, CD19⁻ and CD3⁻ NK cell fraction from Example 7 was cultured as follows:
- (a) Contacting 1×10⁶/mL CD14⁻CD19⁻CD3⁻ initial cells with a composition comprising AIM-V medium, HPL (concentration: 4% w/w), IL-15 (concentration: 30 ng/mL), IL-12 (concentration: 3 ng/mL) and IL-18 (concentration: 50 ng/mL) on day 0.
- (b) Harvesting and spinning down half of the initial cells in step (a), followed by re-suspending cell pellet with a composition comprising AIM-V medium, HPL, IL-15 and IL-12 on day 6.
- (c) Collecting all of the cultured cells in step (b) on day 12.

Optionally, the composition for culturing the cells may be replaced with a fresh medium, with the same constituents on day 0 and day 6, respectively, on day 3 and day 9. for example, the initial cell may be cultured as follows:
- (a) Contacting 1×10⁶/mL CD14⁻CD19⁻CD3⁻ NK cells with a composition comprising AIM-V medium, HPL (concentration: 4% w/w), IL-15 (concentration: 30 ng/mL), IL-12 (concentration: 3 ng/mL) and IL-18 (concentration: 50 ng/mL) on day 0.
- (b) Replacing a medium with the composition comprising AIM-V medium, HPL, IL-15, IL-12 and IL-18 on day 3.
- (c) Harvesting and spinning down half of the cultured cells in step (b), followed by re-suspending cell pellet with a composition comprising AIM-V medium, 4% w/w HPL, 30 ng/mL of IL-15 and 3 ng/mL of IL-12 on day 6.
- (d) Replacing a medium with the composition comprising AIM-V medium, HPL, IL-15, and IL-12 on day 9.
- (e) Collecting all of the cultured cells in step (d) on day 12.

Alternatively, the composition for culturing the cells may be replaced with a fresh medium, with the same constituents on day 0 and day 6, respectively, on day 3 and day 9. for example, the initial cell may be cultured as follows:
- (a) Contacting 1×10⁶/mL CD14⁻CD19⁻CD3⁻ NK cells with a composition comprising AIM-V medium, HPL (concentration: 4% w/w), IL-15 (concentration: 30 ng/mL), IL-12 (concentration: 3 ng/mL) and IL-18 (concentration: 50 ng/mL) on day 0.
- (b) Replacing a medium with the composition comprising AIM-V medium, HPL, IL-15, IL-12 and IL-18 on day 3.
- (c) Harvesting and spinning down half of the cultured cells in step (b), followed by re-suspending cell pellet with a composition comprising AIM-V medium, 4% w/w HPL, 30 ng/mL of IL-15, 3 ng/mL of IL-12 and 50 ng/mL of IL-18 on day 6.
- (d) Replacing a medium with the composition comprising AIM-V medium, HPL, IL-15, IL-12 and IL-18 on day 9.
- (e) Collecting all of the cultured cells in step (d) on day 12.

The cultured cells in step (e) were assayed for their phenotype using Navios Flow Cytometer (10 COLORS/3 LASERS, serial number: AW40325, Beckman Coulter, Inc. USA), Kazula software version 2.1 (Beckman Coulter, Inc. USA) and antibodies listed in Table 5.

TABLE 5

Reagents used for cultivation functional assay and phenotyping of the modified NK cells

| Name | Cat. # | Vender |
|---|---|---|
| Cultivation | | |
| Phosphate-Buffered Saline, 1X without Ca²⁺ and Mg²⁺ | 21-040-CV | Corning |
| CliniMACS PBS/EDFA Buffer | 700-25 | Miltenyi biotec |
| CTS ™ AIM V Serum Free Medium | 0870112DK | Gibco |
| GMP UltraGRO-Advanced | HPCFDCGL05 | AventaCell |
| Ficoll-paque Premium 1.077 | 17-5442-03 | GE Healthcare |
| Streptavidin Microbeads | 130-048-101 | Miltenyi biotec |
| R&D GMP, Human, IL-15 | 247-GMP-025 | R&D |
| R&D GMP, Human, IL-12 | 219-GMP-025 | R&D |
| Human, IL-18, 100 μg | 592106 | BioLegend |
| R&D GMP, Human, IFN-γ | 285-GMP-100 | R&D |
| CD3 Biotin | 300404 | Biolegend |
| CD14 Biotin | 325624 | Biolegend |
| CD19 Biotin | 302204 | Biolegend |
| Functional assay | | |
| CTS ™ AIM V Serum Free Medium | 0870112DK | Gibco |
| GMP UltraGRO-Advanced | HPCFDCGL05 | AventaCell |
| Human, IL-2 | 589108 | BioLegend |
| Human, IL-15, 500 μg | 570308 | BioLegend |
| Killing assay Kit (PanToxiLux ™) | PTL8028 | OncoImmunin |
| CellTrace ™ CFSE Cell Proliferation Kit | C34554 | Molecular probes |
| LEAF ™ Purified-anti human CD3 | 317304 | Biolegend |
| LEAF ™ Purified anti-human CD28 | 302914 | BioLegend |
| CD3-APC-Alexa Flour 750 | A66329 | Beckman Coulter |
| CD8a--Pacific Blue | 301023 | BioLegend |
| Phenotype | | |
| CD86-Alexa flour 488 | 305414 | BioLegend |
| Mouse IgG2b,κ isotype control-Alexa flour 488 | 400329 | BioLegend |
| CD314(NKG2D)-PE | A08934 | Beckman Coulter |
| Beckman Mouse IgG1 isotype control-PE | IM0670U | Beckman Coulter |
| CD83-PE/Cy5 | 305310 | Biolegend |
| mouse IgG1, κ Isotype control-PE/Cy5 | 400116 | Biolegend |
| CD16-PE-Cy7 | 6607118 | Beckman Coulter |
| CD11c-APC | 301614 | BioLegend |
| mouse IgG1, κ Isotype control-APC | 400122 | BioLegend |
| CD56-APC Alexa Flour 700 | B10822 | Beckman Coulter |
| CD3-APC-Alexa Flour 750 | A66329 | Beckman Coulter |
| CD14-APC-Alexa Flour 750 | A86052 | Beckman Coulter |
| CD19-Alexa Flour 750 | A78838 | Beckman Coulter |
| HLA-A,B,C-Pacific Blue | 311418 | BioLegend |
| HLA-DR-Krome Orange | B00070 | Beckman Coulter |
| IgG1-Krome Orange | A96415 | Beckman Coulter |
| CD25-PerCP/Cyanine5.5 | 302626 | BioLegend |

Figure 8:
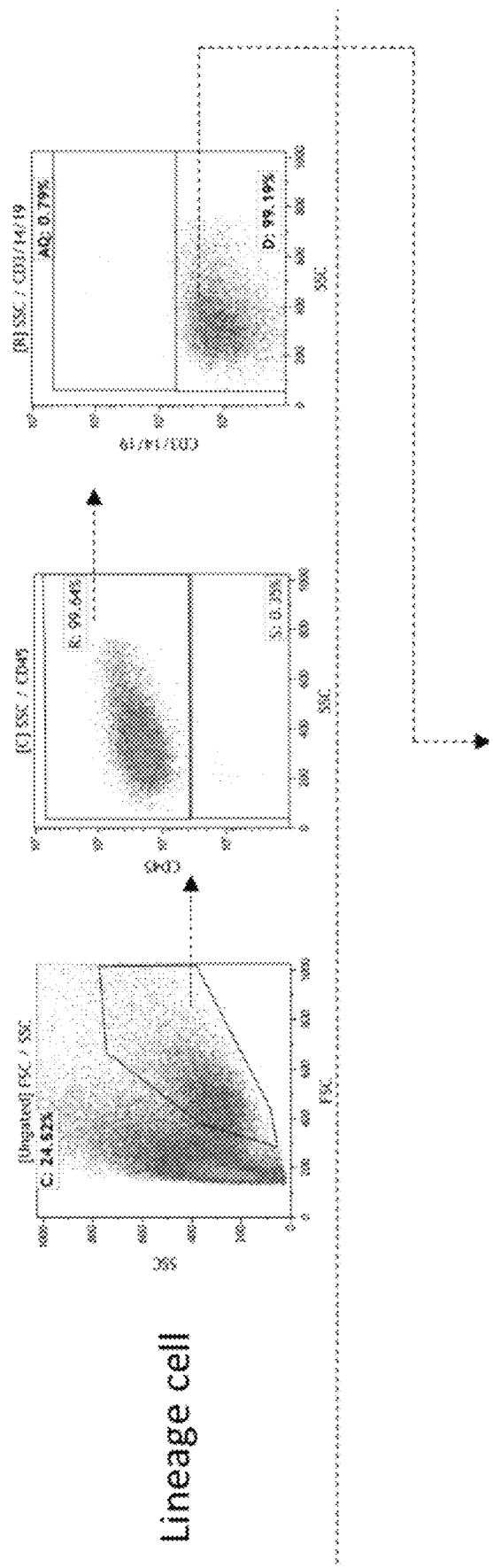
FIG. 8 is a phenotypic analysis of the modified NK cells in accordance with an embodiment of the present application.
Figure 8:
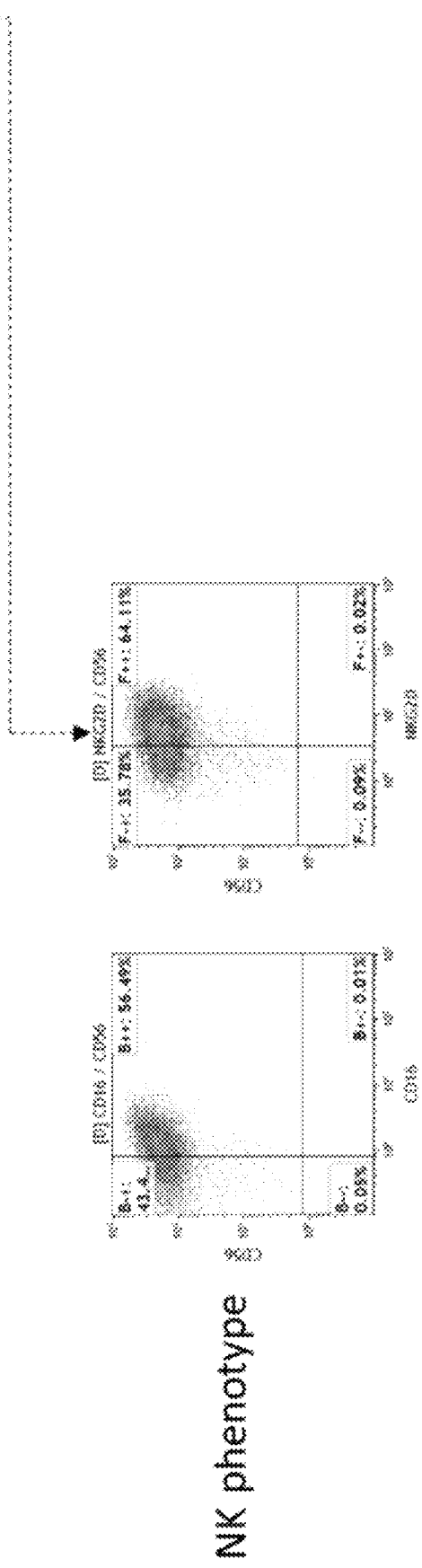
Figure 8:
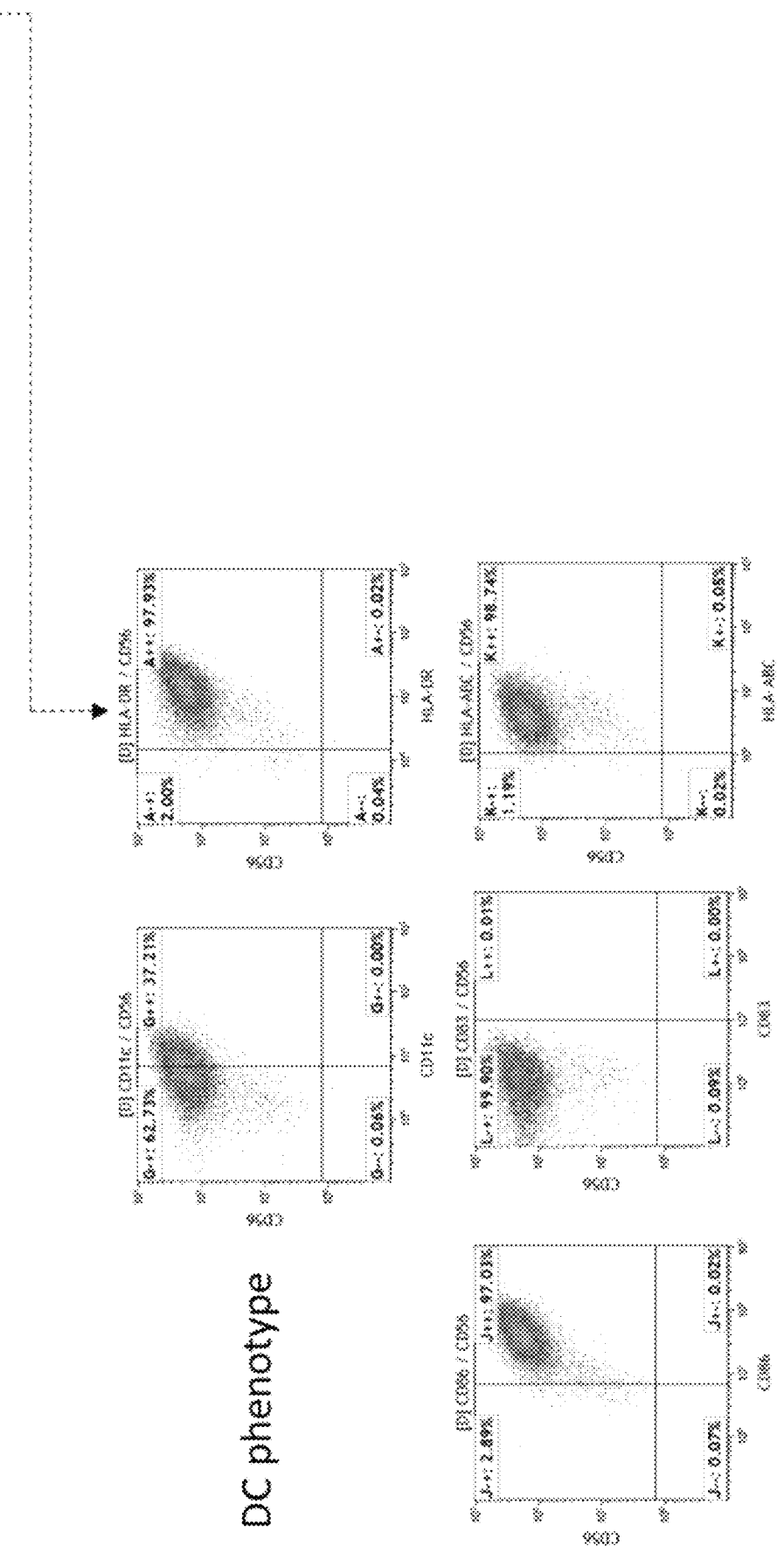

Results: As shown in FIG. 8, the obtained modified NK cells have the NK and DC related phenotypes of CD3⁻CD19⁻CD14⁻CD56^hi CD16^dim NKG2D⁺CD11c⁺CD86⁺HLA-DR⁺CD83⁻.

Example 9: Determination of the Functionality of NK Cells

"Killing" Assay

Evaluation of cytotoxicity of the modified NK cells from Example 8 was performed by PanToxilux kit (OncoImmunin, Inc.). Human chronic myelogenous leukemia (CML) cell line, K562, served as a target cell and stained with TFL4 under the optimal concentration for 50 minutes. Co-incubation of TFL-4 labeled target cell and the modified NK cells with the caspase substrate under 37° C. for 20 minutes. The cells were harvested and analyzed the signal of TFL-4⁺ substrate⁺ via flow cytometry. A positive cells for caspase is indicative of killing.

Figure 9A:
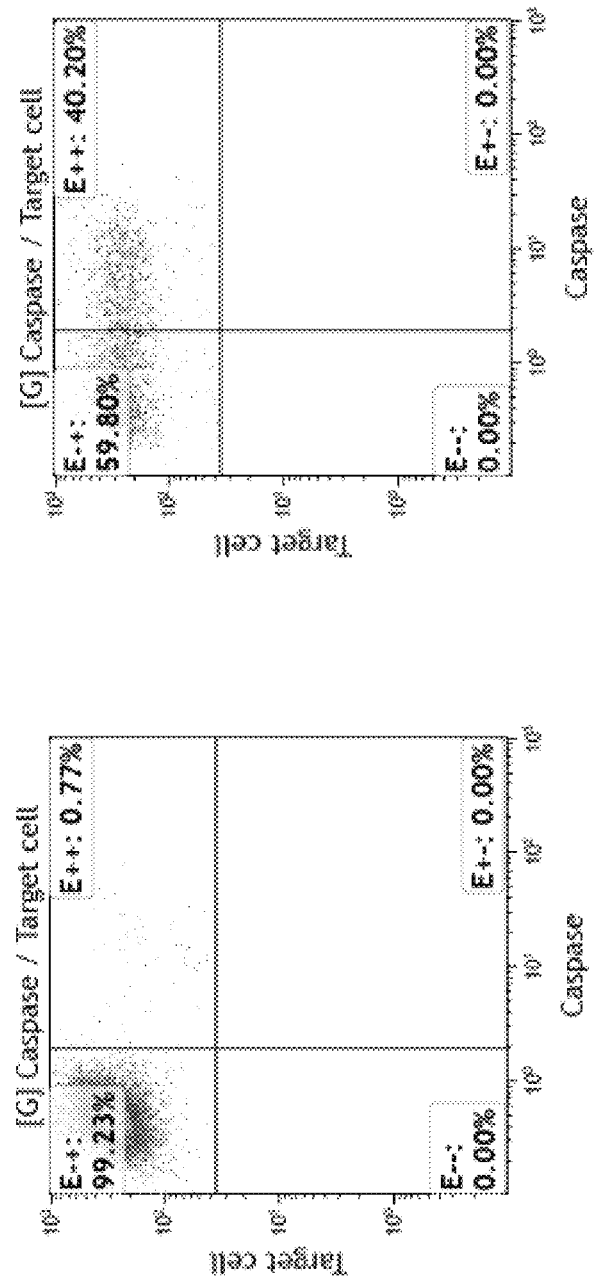
FIG. 9A illustrates the cytotoxicity mediated by the modified NK cell in accordance with an embodiment of the present application.

Results: As shown in FIG. 9A, the percentage of caspase positive target cells (without modified NK cells) was 0.77%, whereas the percentage of caspase positive target cells (with modified NK cells) was 40.2%. This result shows the modified NK cells has a cytotoxic effect on the leukemia target cells K562.

Assay of Antigen-Presenting Activity

Evaluation of the activity of antigen-presentation of the modified NK cells from Example 8 was performed by mixed lymphocyte reaction (MLR). Responder cells (CD25$^-$ PBMCs) were enriched and stained with CellTrace™ CFSE cell proliferation kit (Invitrogen). Co-culture of CSFE-labeled CD25$^-$ PBMCs and the modified NK cells under 37° C. for 5 days. hIL-2 and hIL-15 were added on day 1 and day 3 to reduce the threshold of TCR engagement. The cells were then harvested and analyzed the CFSE-diluted pattern via flow cytometry.

Figure 9B:
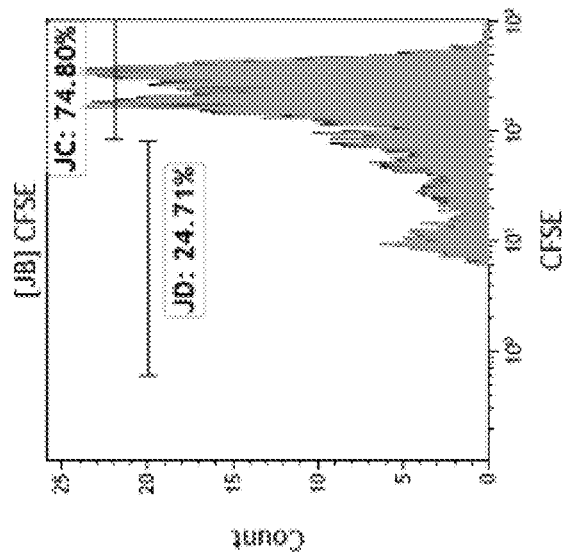
FIG. 9B illustrates the APC activities mediated by the modified NK cell in accordance with an embodiment of the present application.
Figure 9B:
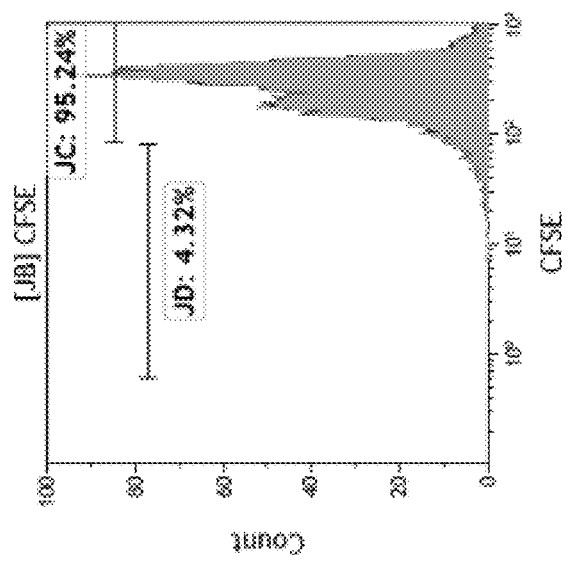

Results: As shown in FIG. 9B, 4.32% of the responder cells were dividing as identified by flow cytometry. However, 24.71% of the cells were dividing in the presence of the modified NK cells from Example 8. This result shows the modified NK cells has an antigen-presentation activity on the CD25$^-$ PBMCs responder cells.

While specific aspects of the invention have been described and illustrated, such aspects should be considered illustrative of the invention only and not as limiting the invention as construed in accordance with the accompanying claims. All publications and patent applications cited in this specification are herein incorporated by reference in their entirety for all purposes as if each individual publication or patent application were specifically and individually indicated to be incorporated by reference for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

What is claimed is:

1. A population of modified natural killer (NK) cells, the modified NK cells comprising:
   a phenotype of CD3$^-$CD19$^-$CD14$^-$CD56$^{hi}$CD16$^{dim}$NKG2D$^+$CD11c$^+$CD86$^+$HLA-DR$^+$CD83$^-$;
   wherein the modified NK cells are obtained by a method comprising
   obtaining a body fluid comprising mononuclear cells;
   contacting the mononuclear cells with a first culturing medium comprising a hematopoietic first cell medium, a first serum protein, IL-15, IL-12 and IL-18 for 3-6 days to obtain a cultured cell population;
   contacting the cultured cell population with a second culturing medium comprising a second hematopoietic cell medium, a second serum protein, IL-15 and IL-12 for 3-6 days after contacting with the first culturing medium; and
   isolating the population of modified NK cells with a phenotype of CD3$^-$CD19$^-$CD14$^-$CD56$^{hi}$CD16$^{dim}$NKG2D$^+$CD11c$^+$CD86$^+$HLA-DR$^+$CD83$^-$ from the cultured cell population;
   wherein the modified NK cells have enhanced cytotoxic properties and dendritic cell (DC) cell function as compared to non-modified NK cells.

2. A pharmaceutical composition, comprising
   (a) the population of modified NK cells of claim 1; and
   (b) a pharmaceutically acceptable carrier or excipient.

3. A method of treating cancer cells, comprising
   administering an effective amount of a composition comprising the population of modified NK cells of claim 1 to a subject in need thereof.

4. The method of claim 3, wherein the effective amount is about $1 \times 10^3$ to about $1 \times 10^9$ cells per dose.

5. The method of claim 3, wherein the population of modified NK cells are autologous or allogeneic.

6. The method of claim 3, wherein the population of modified NK cells are derived from the body fluid including peripheral blood, cord blood or bone marrow.

7. The method of claim 3, further comprising expanding the population of modified NK cell in vitro.

8. A method of culturing a population of modified natural killer (NK) cells, comprising
   obtaining a body fluid comprising mononuclear cells;
   contacting the mononuclear cells with a first culturing medium comprising a first hematopoietic cell medium, a first serum protein, IL-15, IL-12 and IL-18 for 3-6 days to obtain a cultured cell population;
   contacting the cultured cell population with a second culturing medium comprising a second hematopoietic cell medium, a second serum protein, IL-15 and IL-12 for 3-6 days after contacting with the first culturing medium; and
   isolating a population of modified NK cells with a phenotype of CD3$^-$CD19$^-$CD14$^-$CD56$^{hi}$CD16$^{dim}$NKG2D$^+$CD11c$^+$CD86$^+$HLA-DR$^+$CD83$^-$ from the cultured cell population;
   wherein the modified NK cells have enhanced cytotoxic properties and dendritic cell function as compared to non-modified NK cells.

9. The method of claim 8, wherein the mononuclear cells are derived from the body fluid including peripheral blood, cord blood or bone marrow.

10. The method of claim 8, wherein the first serum protein comprises a human platelet lysate.

11. The method of claim 8, wherein the second serum protein comprises a human platelet lysate.

12. The method of claim 8, further comprising negative selecting the mononuclear cells for cells with a phenotype of CD3$^-$CD14$^-$CD19$^-$ prior to contacting with the first culturing medium.

* * * * *